(12) United States Patent
Brokman et al.

(10) Patent No.: US 11,527,001 B2
(45) Date of Patent: *Dec. 13, 2022

(54) SYSTEMS AND METHODS FOR REGISTERING IMAGES OBTAINED USING VARIOUS IMAGING MODALITIES AND VERIFYING IMAGE REGISTRATION

(71) Applicants: Omer Brokman, Tirat Carmel (IL); Oleg Prus, Haifa (IL); Eyal Zadicario, Tel Aviv-Jaffa (IL)

(72) Inventors: Omer Brokman, Tirat Carmel (IL); Oleg Prus, Haifa (IL); Eyal Zadicario, Tel Aviv-Jaffa (IL)

(73) Assignee: INSIGHTEC, LTD., Tirat Carmel (IL)

( * ) Notice: Subject to any disclaimer, the term of this patent is extended or adjusted under 35 U.S.C. 154(b) by 9 days.

This patent is subject to a terminal disclaimer.

(21) Appl. No.: 17/104,450

(22) Filed: Nov. 25, 2020

(65) Prior Publication Data
US 2021/0097702 A1    Apr. 1, 2021

Related U.S. Application Data

(63) Continuation of application No. 15/155,171, filed on May 16, 2016, now Pat. No. 10,878,586, which is a
(Continued)

(51) Int. Cl.
*G06T 7/30*    (2017.01)
*A61B 6/03*    (2006.01)
(Continued)

(52) U.S. Cl.
CPC .............. *G06T 7/30* (2017.01); *A61B 5/0035* (2013.01); *A61B 5/055* (2013.01); *A61B 6/032* (2013.01);
(Continued)

(58) Field of Classification Search
CPC ...... A61B 2017/0011; A61B 2090/374; A61B 6/488; A61B 8/5261; A61B 8/5276;
(Continued)

(56) References Cited

U.S. PATENT DOCUMENTS 5,749,362 A    5/1998  Funda
8,965,072 B2   2/2015  Fujii et al.
(Continued)

FOREIGN PATENT DOCUMENTS

EP    3272395 A1   1/2018
JP    6448908 B2   2/1989
(Continued)

OTHER PUBLICATIONS

International Search Report, for International Application No. PCT/IB2016/056016 dated Jul. 4, 2017, 16 pages.
(Continued)

*Primary Examiner* — Pinalben Patel
(74) *Attorney, Agent, or Firm* — Morgan, Lewis & Bockius LLP

(57) ABSTRACT

Embodiments of the present invention provide systems and methods to detect a moving anatomic feature during a treatment sequence based on a computed and/or a measured shortest distance between the anatomic feature and at least a portion of an imaging system.

9 Claims, 17 Drawing Sheets

Related U.S. Application Data continuation of application No. 14/879,235, filed on Oct. 9, 2015, now Pat. No. 9,934,570.

(51) Int. Cl.

| | | |
|---|---|---|
| *A61B 5/055* | (2006.01) | |
| *A61B 6/12* | (2006.01) | |
| *A61B 8/00* | (2006.01) | |
| *A61B 8/08* | (2006.01) | |
| *A61B 6/00* | (2006.01) | |
| *A61B 5/00* | (2006.01) | |
| *G06T 7/70* | (2017.01) | |
| *A61N 7/02* | (2006.01) | |
| *G06T 7/00* | (2017.01) | |
| *G06T 7/32* | (2017.01) | |
| *G06T 3/00* | (2006.01) | |
| *G06T 7/20* | (2017.01) | |
| *G06T 11/00* | (2006.01) | |
| *G06T 15/50* | (2011.01) | |
| *G01R 33/56* | (2006.01) | |
| *A61B 17/00* | (2006.01) | |
| *G01R 33/48* | (2006.01) | |
| *A61B 90/00* | (2016.01) | |

(52) U.S. Cl.
CPC ............... *A61B 6/12* (2013.01); *A61B 6/488* (2013.01); *A61B 6/5247* (2013.01); *A61B 8/4209* (2013.01); *A61B 8/4416* (2013.01); *A61B 8/4483* (2013.01); *A61B 8/5261* (2013.01); *A61B 8/5276* (2013.01); *A61N 7/02* (2013.01); *G06T 3/0068* (2013.01); *G06T 7/0014* (2013.01); *G06T 7/20* (2013.01); *G06T 7/32* (2017.01); *G06T 7/70* (2017.01); *G06T 11/006* (2013.01); *G06T 15/503* (2013.01); *A61B 2017/0011* (2013.01); *A61B 2090/364* (2016.02); *A61B 2090/374* (2016.02); *A61B 2090/3762* (2016.02); *G01R 33/4814* (2013.01); *G01R 33/5608* (2013.01); *G06T 2207/10081* (2013.01); *G06T 2207/10088* (2013.01); *G06T 2207/10132* (2013.01); *G06T 2207/20221* (2013.01)

(58) Field of Classification Search
CPC ... A61B 8/4416; A61B 5/0035; A61B 6/5247; A61B 8/4209; A61B 6/12; A61B 2090/3762; A61B 2090/364; A61B 8/4483; A61B 6/032; G06T 2207/10081; G06T 2207/20221; G06T 2207/10088; G06T 7/0014; G06T 2207/10132; G06T 3/0068; G06T 7/30; G06T 11/006; G06T 7/70; G06T 7/20; G06T 7/32; G06T 15/503; G01R 33/4814; A61N 7/02
See application file for complete search history.

(56) References Cited

U.S. PATENT DOCUMENTS

| | | | |
|---|---|---|---|
| 9,439,623 B2 | 9/2016 | Frank et al. | |
| 9,934,570 B2 * | 4/2018 | Brokman | A61B 8/4209 |
| 10,631,825 B2 | 4/2020 | Lee et al. | |
| 2006/0002630 A1 | 1/2006 | Fu et al. | |
| 2008/0292194 A1 | 11/2008 | Schmidt et al. | |
| 2010/0239144 A1 | 9/2010 | Fichtinger et al. | |
| 2012/0022546 A1 | 1/2012 | Hubschman | |
| 2012/0033868 A1 * | 2/2012 | Ren | A61B 6/025 378/21 |
| 2012/0155734 A1 | 6/2012 | Barratt et al. | |
| 2013/0120453 A1 | 5/2013 | Carmi | |
| 2013/0195338 A1 | 8/2013 | Xu et al. | |
| 2013/0266178 A1 | 10/2013 | Jain | |
| 2013/0322726 A1 | 12/2013 | Nathaniel | |
| 2014/0029812 A1 | 1/2014 | Kriston et al. | |
| 2014/0056502 A1 | 2/2014 | Twellmann et al. | |
| 2014/0064584 A1 | 3/2014 | Schmidt | |
| 2014/0121013 A1 | 7/2014 | Han | |
| 2014/0212014 A1 | 7/2014 | Kim et al. | |
| 2014/0323845 A1 | 10/2014 | Forsberg | |
| 2015/0265236 A1 | 9/2015 | Garner et al. | |
| 2015/0282890 A1 * | 10/2015 | Cohen | A61B 5/7289 600/424 |
| 2015/0289829 A1 | 10/2015 | Yamada et al. | |
| 2015/0310296 A1 | 10/2015 | Seki et al. | |
| 2015/0320399 A1 | 11/2015 | Chono | |
| 2015/0371361 A1 | 12/2015 | Kim et al. | |
| 2016/0000515 A1 | 1/2016 | Sela | |
| 2016/0078633 A1 | 3/2016 | Tahmasebi Maraghoosh et al. | |
| 2016/0110862 A1 | 4/2016 | Kim et al. | |
| 2016/0217560 A1 | 7/2016 | Tahmasebi Maraghoosh et al. | |
| 2016/0302747 A1 | 10/2016 | Averbuch | |
| 2016/0310761 A1 | 10/2016 | Li et al. | |
| 2017/0091939 A1 | 3/2017 | Kluckner et al. | |
| 2017/0103540 A1 | 4/2017 | Brokman et al. | |
| 2017/0164835 A1 * | 6/2017 | Wiest | G01S 15/8997 |
| 2017/0319165 A1 | 11/2017 | Averbuch | |
| 2018/0325604 A1 * | 11/2018 | Atarot | A61B 1/3132 |

FOREIGN PATENT DOCUMENTS

| | | |
|---|---|---|
| JP | 2014171870 A | 9/2014 |
| WO | 2011070477 A1 | 6/2011 |

OTHER PUBLICATIONS

Hynynen et al., "Pre-clinical testing of a phased array ultrasound system for MRI-guided noninvasive surgery of the brain—A primate study", European Journal or Radiology 59 (2006), pp. 149-156.

McDannold et al., "Transcranial MRI-guided focused ultrasound surgery of brain tumors: Initial findings in three patients", Neurosurgery (2010) 66(2): 323-332.

Ezekiel Maloney et al., "Emerging HIFU applications in cancer therapy," International Journal of Hyperthermia, vol. 31, No. 3, Nov. 4, 2014, pp. 302-309, XP055648951, 9 pgs.

Insightec Ltd., Extended European Search Report, EP19189187.8, dated Dec. 16, 2019, 7 pgs.

Vincent Auboiroux et al., "Ultrasonography-based 2D motion-compensated HIFU sonication integrated with reference-free MR temperature monitoring: a feasibility study ex vivo," Physics in Medicine and Biology, Institute of Physics Publishing, Bristol GB, vol. 57, No. 10, Apr. 20, 2012, pp. N159-N171, XP020221947, 15 pgs.

* cited by examiner

SYSTEMS AND METHODS FOR REGISTERING IMAGES OBTAINED USING VARIOUS IMAGING MODALITIES AND VERIFYING IMAGE REGISTRATION

CROSS-REFERENCE TO RELATED APPLICATION

This application is a continuation of U.S. Ser. No. 15/155,171 (filed on May 16, 2016), which is a continuation of U.S. Ser. No. 14/879,235 (now U.S. Pat. No. 9,934,570); the entire disclosures of these priority documents are hereby incorporated by reference in their entireties.

FIELD OF THE INVENTION

The present invention relates to imaging, and, more specifically, to systems and methods for registering images and/or verifying image registrations obtained using various imaging modalities.

BACKGROUND

Medical imaging of internal organs provides important anatomic and diagnostic information, which medical personnel can employ to make therapeutic decisions. Medical images can be acquired using various non-invasive imaging procedures, such as computed topography (CT), magnetic resonance imaging (MRI), or ultrasound imaging. A CT system transmits x-rays through an anatomic site of interest, and based on the attenuation coefficients of the x-rays, cross-sectional images ("slices") of the object can be reconstructed. As a result, the CT system is well suited for viewing details about bony structures, diagnosing diseases of the lung and chest, and detecting cancers. Advantages of CT imaging also include, for example, a short scan time for a complete scan (typically less than five minutes), low cost (about half the price of an MRI apparatus), the ability to accurately outline bony tissue inside the body, fewer motion artifacts due to fast imaging speeds (each scan time is less than 30 seconds), etc. CT systems, however, irradiate the patient and pose consequent risk; for this reason, CT scans are not recommended for pregnant women or children.

Ultrasound imaging, which involves passing high-frequency acoustic waves through the body, is another widely used technique. Ultrasound waves penetrate well through soft tissues and, due to their short wavelengths, can be focused to spots with dimensions of a few millimeters. In a typical ultrasound examination, a transducer probe is placed directly on the skin or inside a body opening. A thin layer of gel may be applied to the skin to provide direct contact between the transducer probe and skin and thereby allow efficient transfer of ultrasound energy into the body. An ultrasound image of internal anatomic structures can be constructed from the waves reflected by those structures—in particular, for example, from the amplitudes and phases of the reflection signals and/or the time it takes for the ultrasound waves to travel through the body. Because ultrasound images are captured in real-time, they can also show movement of the body's internal organs as well as blood flowing through the blood vessels. In addition, ultrasound imaging offers high temporal resolution, high sensitivity to acoustic scatterers (such as calcifications and gas bubbles), excellent visualization, low cost, portability, and no ionizing radiation exposure, and is thus generally considered safe even for pregnant women and children.

MRI is still another imaging modality that is used to visualize the target tissue; MRI can be used in conjunction with ultrasound to guide the ultrasound focus during therapy as further described below. In brief, MRI involves placing a patient into a homogeneous static magnetic field, thus aligning the spins of hydrogen nuclei in the tissue. Then, by applying a radio-frequency (RF) electromagnetic pulse of the right frequency (the "resonance frequency"), the spins may be flipped, temporarily destroying the alignment and inducing a response signal. Different tissues produce different response signals, resulting in a contrast among these tissues in MR images. Because the resonance frequency and the frequency of the response signal depend on the magnetic field strength, the origin and frequency of the response signal can be controlled by superposing magnetic gradient fields onto the homogeneous field to render the field strength dependent on position. By using time-varying gradient fields, MRI "scans" of the tissue can be obtained.

Many MRI protocols utilize time-dependent gradients in two or three mutually perpendicular directions. The relative strengths and timing of the gradient fields and RF pulses are specified in a pulse sequence. Time-dependent magnetic field gradients may be exploited, in combination with the tissue dependence of the MRI response signal, to visualize, for example, a brain tumor, and determine its location relative to the patient's skull. MRI has advantages including multi-planar imaging capability (without moving the patient), high signal-to-noise ratio, high sensitivity to subtle changes in soft tissue morphology and function, and no radiation exposure. But MRI suffers from its sensitivity to patient movement due to the long scan time (typically between 30 minutes to a few hours), lower-resolution images of bony structures, and interference from the operation of other radio-frequency (RF) devices.

Because each imaging technique has its own strengths and weaknesses and may provide different types of information, it may be advantageous in practice to combine different imaging techniques. For example, combining a CT scan with MRI can provide good details about bony structures as well as subtle differences between soft tissues. A combination of MRI and ultrasound imaging has been shown to provide additional diagnostic information for better diagnosis in intraoperative neurosurgical applications and breast biopsy guidance. Further, because ultrasound energy can be employed therapeutically—e.g., to heat and ablate diseased (e.g., cancerous) tissue without causing significant damage to surrounding healthy tissue—the combination of MRI and ultrasound provides imaging capability during therapeutic medical procedures. An ultrasound focusing system generally includes an acoustic transducer surface, or an array of transducer surfaces, to generate one or more ultrasound beams. In transducer arrays, the individual surfaces, or "elements," are typically individually controllable—i.e., their vibration phases and/or amplitudes can be set independently of one another—allowing the beam to be steered in a desired direction and focused at a desired distance. The ultrasound system often also includes receiving elements, integrated into the transducer array or provided in form of a separate detector, that help monitor ultrasound-based treatment. For example, the receiving elements may detect ultrasound reflected by interfaces between the transducer and the target tissue, which may result from air bubbles on the skin that need to be removed to avoid skin burns. The receiving elements may also be used to detect cavitation in overheated tissues (i.e., the formation of cavities due to the collapse of bubbles formed in the liquid of the tissue).

A focused ultrasound transducer system may include MR tracking coils or other markers for determining the transducer position and orientation relative to the target tissue (such as a tumor) in the MR image. Based on computations of the required transducer element phases and amplitudes, the transducer array is then driven so as to focus ultrasound at the target. The ultrasound focus itself may be visualized using MRI or acoustic resonance force imaging (ARFI), and such visualization may be used to adjust the focus position. These methods are generally referred to as magnetic-resonance-guided focusing of ultrasound (MRgFUS).

To successfully integrate two or more imaging systems and/or combine information provided by distinct systems, it is necessary to register image data that may be obtained in different imaging coordinate systems. Conventional approaches to registration typically involve complex computational procedures and may not provide sufficient accuracy for therapeutic purposes. For this reason, utilizing such image registration without verification may result in an inaccurate application of energy and unsuccessful or lengthy treatment. Accordingly, there is a need for establishing and verifying registration of images obtained using different modalities in a sufficiently fast, reliable manner to support therapeutic applications.

SUMMARY

Embodiments of the present invention provide systems and methods to evaluate and quantify the accuracy of image registration obtained using different modalities and in different coordinate systems. In various embodiments, the accuracy of the image registration relating two imaging coordinate systems (such as a CT system and an MRI system) is evaluated via the use of a third imaging modality (such as an ultrasound system). For example, the spatial relationship between the ultrasound coordinate system and the MRI coordinate system can be determined by obtaining an MR image that includes at least a portion of the ultrasound system (e.g., some of the transducer elements) in conjunction with the known spatial arrangement of the portion of the ultrasound system included in the MR image. Next, the coordinates of a previously acquired CT image of an anatomic region of interest may be transformed to coordinates in the MRI system using the image registration under study. Consequently, a distance between the anatomic region of interest and the ultrasound system may be computed in the MRI coordinate system. This distance may also be acoustically measured using the ultrasound system, and the measured distance in the ultrasound coordinate system may subsequently be transformed to the MRI coordinate system. By comparing the computed and measured distances in the MRI coordinate system, an error vector can be assigned based on the discrepancy therebetween. This error vector indicates the accuracy of the image registration under study—i.e., a smaller error vector indicates a smaller deviation of the computed distance from the measured distance and thus a higher registration accuracy. It should be stressed, of course, that this exemplary use of imaging modalities is for illustrative purposes only, and that any three modalities may be used (with any of the modalities functioning in any of the described roles) as appropriate to the application.

In some embodiments, the present invention also provides an approach for registering images (as opposed to verifying their registration) obtained in the distinct coordinate systems of two imaging modalities (e.g., a CT system and an MRI system) using a third modality (e.g., an ultrasound system). For example, the ultrasound coordinate system may be first registered with the MRI coordinate system via the use of an MR image of at least a portion of the ultrasound system and the known spatial arrangement of the ultrasound system as described above. Registration between the ultrasound coordinate system and CT coordinate system may be established via an ultrasound image and a CT image of the anatomic target of interest. Subsequently, the MRI and CT coordinate systems may be registered using the image registration relating the ultrasound and MRI coordinate systems and the image registration relating the ultrasound and CT coordinate systems.

Although the present invention has been described with reference to the use of the an ultrasound system for verifying and/or obtaining image registration between the MRI and CT coordinate systems, it is not intended that such details should be regarded as limitations upon the scope of the invention. For example, as noted above, the MRI coordinate system may be used to register the ultrasound and CT coordinate systems, and the CT system may be used to register the ultrasound and MRI systems. Moreover, image registrations between other imaging coordinate systems may also be evaluated and/or acquired by performing the approaches described herein.

Accordingly, in one aspect, the invention pertains to a method for verifying registration of images of an internal anatomic target obtained using a first imaging system and a second imaging system. In various embodiments, the method includes (a) acquiring a first image of the anatomic target and at least a portion of a third imaging system using the first imaging system; (b) measuring a distance between the third imaging system and the anatomic target using the third imaging system; (c) acquiring a second image of the anatomic target using the second imaging system; (d) registering the first image and the second image using the registration; and (e) based on (i) positions of the at least a portion of the third imaging system and the anatomic target in the first image and (ii) the measured distance, computing an error in the registration. In one implementation, the first, second, and third imaging systems include an MRI system, a CT system, and an ultrasound transducer system, respectively.

The method may further include obtaining the positions of the at least a portion of the third imaging system in the coordinate system of the third imaging system; the positions may be determined based on a time-of-flight method. In addition, the method may include computing a transformation relating the coordinate system of the first imaging system and the coordinate system of the third imaging system based on the positions of the at least a portion of the third imaging system in the first image and in the coordinate system of the third imaging system. In one embodiment, the positions of the third imaging system are transformed from the coordinate system of the third imaging system to the coordinate system of the first imaging system. The second image of the anatomic target is transformed from the coordinate system of the second imaging system to the coordinate system of the first imaging system. Additionally, the distance between the third imaging system and the anatomic target is computed based on the transformed positions of the third imaging system and transformed second image in the coordinate system of the first imaging system.

The distance between the third imaging system and the anatomic target may be measured based on signals transmitted from and received by the third imaging system. In various embodiments, the method further includes transforming the measured distance from the coordinate system of the third imaging system to the coordinate system of the first imaging system. The error of the registration is then determined based on a deviation of the transformed measured distance from the computed distance. In one implementation, the error of the registration is compared to a predetermined threshold and the validity of the registration is determined based on the comparison.

In another aspect, the invention relates to a system for verifying registration of images of an internal anatomic target obtained using a first imaging system and a second imaging system. In some embodiments, the system includes the first imaging system for acquiring a first image of the anatomic target and at least a portion of a third imaging system; the second imaging system for acquiring a second image of the anatomic target; and a controller in communication with the first, second, and third imaging systems. In one implementation, the controller is configured to measure a distance between the third imaging system and the anatomic target; register the first image and the second image; and compute an error in the registration based on (i) positions of the at least a portion of the third imaging system and the anatomic target in the first image and (ii) the measured distance. The first, second, and third imaging systems may include an MRI system, a CT system, and an ultrasound transducer system, respectively.

The controller may be further configured to determine the positions of the at least a portion of the third imaging system in the coordinate system of the third imaging system; the positions may be determined based on a time-of-flight method. In addition, the controller may be configured to compute a transformation relating the coordinate system of the first imaging system and the coordinate system of the third imaging system based on the positions of the at least a portion of the third imaging system in the first image and in the coordinate system of the third imaging system. In one embodiment, the controller transforms positions of the third imaging system from the coordinate system of the third imaging system to the coordinate system of the first imaging system. The controller transforms the second image of the anatomic target from the coordinate system of the second imaging system to the coordinate system of the first imaging system. Additionally, the controller is configured to compute the distance between the third imaging system and the anatomic target based on the transformed positions of the third imaging system and transformed second image in the coordinate system of the first imaging system.

Further, the controller may be configured to measure the distance between the third imaging system and the anatomic target based on signals transmitted from and received by the third imaging system. The controller may transform the measured distance from the coordinate system of the third imaging system to the coordinate system of the first imaging system. In addition, the controller may determines the error of the registration based on a deviation of the transformed measured distance from the computed distance, compare the error of the registration to a predetermined threshold, and determine validity of the registration based on the comparison.

Another aspect of the invention relates to a method for registering images of an internal anatomic target obtained using a first imaging system and a second imaging system. In various embodiments, the method includes (a) acquiring a first image of the anatomic target and at least a portion of a third imaging system using the first imaging system; (b) acquiring a second image of the anatomic target using the second imaging system; (c) acquiring a third image of the anatomic target using the third imaging system; (d) registering the second image and the third image; (e) based on (i) positions of the at least a portion of the third imaging system and the anatomic target in the first image and (ii) the registered second and third images, computing transformations relating a coordinate system of the first imaging system, a coordinate system of the second imaging system, and a coordinate system of the third imaging system. In one implementation, the first, second, and third imaging systems include an MRI system, a CT system, and an ultrasound transducer system, respectively.

The registration of the second image and the third image may include transforming coordinates associated with the internal anatomic target in the coordinate system of the second imaging system to coordinates in the coordinate system of the third imaging system. For example, the coordinates associated with the internal anatomic target in the coordinate system of the second imaging system may be fitted to the coordinates associated with the internal anatomic target in the coordinate system of the third imaging system.

In addition, the method may include obtaining the positions of the at least a portion of the third imaging system in the coordinate system of the third imaging system. In one embodiment, the positions are determined based on a time-of-flight method. The method may include computing the transformation relating the coordinate system of the first imaging system and the coordinate system of the third imaging system based on the positions of the at least a portion of the third imaging system in the first image and in the coordinate system of the third imaging system. In some embodiments, the transformation relating the coordinate system of the first imaging system and the coordinate system of the third imaging system is computed based on the transformation relating the coordinate system of the first imaging system and the coordinate system of the third imaging system.

In yet another aspect, the invention pertains to a system for registering images of an internal anatomic target obtained using a first imaging system and a second imaging system. In some embodiments, the system includes the first imaging system for acquiring a first image of the anatomic target and at least a portion of a third imaging system; the second imaging system for acquiring a second image of the anatomic target; the third imaging system for acquiring a third image of the anatomic target using; and a controller in communication with the first, second, and third imaging systems. In one implementation, the controller is configured to register the second image and the third image; and compute transformations relating a coordinate system of the first imaging system, a coordinate system of the second imaging system, and a coordinate system of the third imaging system based on (i) positions of the at least a portion of the third imaging system and the anatomic target in the first image and (ii) the registered second and third images. The first, second, and third imaging systems may include, for example, an MRI system, a CT system, and an ultrasound transducer system, respectively.

The controller may be further configured to transform coordinates associated with the internal anatomic target in the coordinate system of the second imaging system to coordinates in the coordinate system of the third imaging system. For example, the controller may fit the coordinates associated with the internal anatomic target in the coordinate system of the second imaging system to the coordinates associated with the internal anatomic target in the coordinate system of the third imaging system.

In addition, the controller may determine the positions of the at least a portion of the third imaging system in the coordinate system of the third imaging system. In one embodiment, the positions are de based on a time-of-flight method. Further, the controller may be configured to compute the transformation relating the coordinate system of the first imaging system and the coordinate system of the third imaging system based on the positions of the at least a portion of the third imaging system in the first image and in the coordinate system of the third imaging system. The controller may be configured to compute the transformation relating the coordinate system of the first imaging system and the coordinate system of the third imaging system based on the transformation relating the coordinate system of the first imaging system and the coordinate system of the third imaging system.

Still another aspect of the invention relates to a method for detecting a moving anatomic feature during a treatment sequence. In various embodiments, the method includes (a) prior to the treatment sequence, (i) acquiring a first image of the anatomic feature and at least a portion of a first imaging system, and (ii) processing the first image to compute a shortest distance between the anatomic feature and the at least a portion of the first imaging system; and (b) during the treatment sequence, (i) measuring the shortest distance between the anatomic feature and the at least a portion of the first imaging system, (ii) comparing the measured shortest distance to the computed shortest distance obtained in step (a) to determine a deviation therefrom, and (iii) determining movement of the anatomic feature based on the deviation. In one implementation, the first image is acquired using a second imaging system; the method further includes acquiring a second image of the anatomic feature using a third imaging system prior to the treatment sequence. The first, second, and third imaging systems include an ultrasound transducer system, an MRI system, and a CT system, respectively.

The method may include obtaining positions of the at least a portion of the first imaging system in a coordinate system of the first imaging system; the positions may be determined based on a time-of-flight method. In addition, the method may include computing a transformation relating the coordinate system of the first imaging system and a coordinate system of the second imaging system based on the positions of the at least a portion of the first imaging system in the first image and in the coordinate system of the first imaging system. In one embodiment, the method further includes transforming the positions of the first imaging system from the coordinate system of the first imaging system to the coordinate system of the second imaging system based on the computed transformation.

In some embodiments, the method includes registering the first image and the second image. Additionally, the method includes transforming the second image of the anatomic feature from a coordinate system of the third imaging system to the coordinate system of the second imaging system. The shortest distance may then be computed based on the transformed positions of the first imaging system and transformed second image in the coordinate system of the second imaging system.

In various embodiments, the shortest distance between the anatomic feature and the at least a portion of the first imaging system is measured based on signals transmitted from and received by the first imaging system. In one implementation, the measured shortest distance is transformed from the coordinate system of the first imaging system to the coordinate system of the second imaging system. Further, the method further includes comparing the deviation to a predetermined threshold and determining movement of the anatomic feature based on the comparison.

In another aspect, the invention relates to a system for detecting a moving anatomic feature during a treatment sequence. In various embodiments, the system includes a first imaging system for acquiring a first image of the anatomic feature and at least a portion of a second imaging system prior to the treatment sequence; and a controller in communication with the first and second systems. In one implementation, the controller is configured to (a) prior to the treatment sequence, process the first image to compute a shortest distance between the anatomic feature and the at least a portion of the second imaging system; and (b) during the treatment sequence, (i) measure the shortest distance between the anatomic feature and the at least a portion of the second imaging system, (ii) compare the measured shortest distance to the computed shortest distance obtained in step (a) to determine a deviation therefrom, and (iii) determine movement of the anatomic feature based on the deviation. The system may further include a third imaging system for acquiring a second image of the anatomic feature prior to the treatment sequence. In one embodiment, the first, second, and third imaging systems include an MRI system, an ultrasound transducer system, and a CT system, respectively.

The controller may be further configured to obtain positions of the at least a portion of the second imaging system in a coordinate system of the second imaging system; the positions may be determined based on a time-of-flight method. In addition, the controller may compute a transformation relating the coordinate system of the second imaging system and a coordinate system of the first imaging system based on the positions of the at least a portion of the second imaging system in the first image and in the coordinate system of the second imaging system. In one embodiment, the controller is configured to transform the positions of the second imaging system from the coordinate system of the second imaging system to the coordinate system of the first imaging system based on the computed transformation.

In some embodiments, the controller is further configured to register the first image and the second image. Additionally, the may transform the second image of the anatomic feature from a coordinate system of the third imaging system to the coordinate system of the first imaging system. The controller may then compute the shortest distance based on the transformed positions of the second imaging system and transformed second image in the coordinate system of the first imaging system.

In various embodiments, the controller is further configured to measure the shortest distance based on signals transmitted from and received by the second imaging system. In one implementation, the controller transforms the measured shortest distance from the coordinate system of the second imaging system to the coordinate system of the first imaging system. Further, the controller compares the deviation to a predetermined threshold and determines movement of the anatomic feature based on the comparison.

In still another aspect, the invention relates to a method for detecting a moving anatomic feature during a treatment sequence having a plurality of treatment periods. In various embodiments, the method includes measuring a shortest distance between the anatomic feature and at least a portion of an imaging system (e.g., an ultrasound transducer system) during the treatment sequence; comparing the measured shortest distance in a current treatment period to the measured shortest distance in a previous treatment period to determine a deviation therefrom; and determining movement of the anatomic feature based on the deviation. The shortest distance between the anatomic feature and the at least a portion of the imaging system may be measured based on signals transmitted from and received by the imaging system. In addition, the method may include comparing the deviation to a predetermined threshold and determining movement of the anatomic feature based on the comparison.

In another aspect, the invention pertains to a system for detecting a moving anatomic feature during a treatment sequence having a plurality of treatment periods. In various embodiments, the system includes an imaging system (e.g., an ultrasound transducer system) for measuring a shortest distance between the anatomic feature and at least a portion of the imaging system during the treatment sequence; and a controller in communication with the imaging system. In one implementation, the controller is configured to compare the measured shortest distance in a current treatment period to the measured shortest distance in a previous treatment period to determine a deviation therefrom; and determine movement of the anatomic feature based on the deviation. The controller may be further configured to measure the shortest distance between the anatomic feature and the at least a portion of the imaging system based on signals transmitted from and received by the imaging system. In addition, the controller may compare the deviation to a predetermined threshold and determine movement of the anatomic feature based on the comparison.

As used herein, the terms "approximately," "roughly," and "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
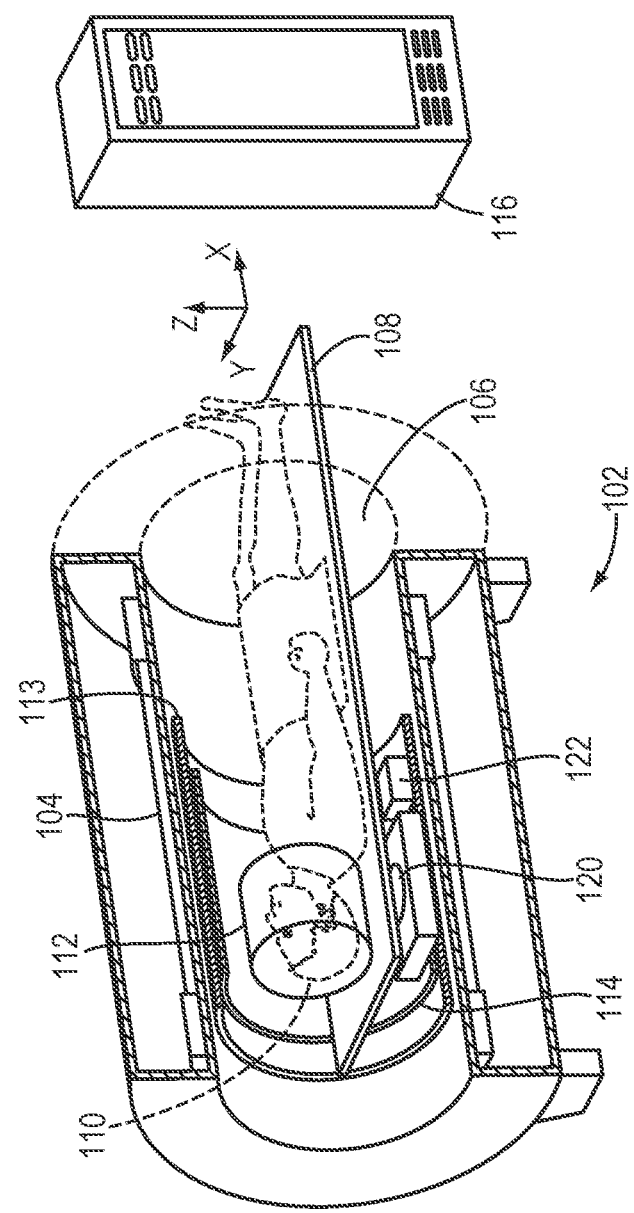
FIG. 1A schematically depicts an exemplary MRI system in accordance with various embodiments of the current invention.

FIG. 1A illustrates an exemplary MRI apparatus 102. The apparatus 102 may include a cylindrical electromagnet 104, which generates the requisite static magnetic field within a bore 106 of the electromagnet 104. During medical procedures, a patient is placed inside the bore 106 on a movable support table 108. A region of interest 110 within the patient (e.g., the patient's head) may be positioned within an imaging region 112 wherein the electromagnet 104 generates a substantially homogeneous field. A set of cylindrical magnetic field gradient coils 113 may also be provided within the bore 106 and surrounding the patient. The gradient coils 113 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 114 surrounding the imaging region 112 emits RF pulses into the imaging region 112 to cause the patient's tissues to emit magnetic-resonance (MR) response signals. Raw MR response signals are sensed by the RF coil 114 and passed to an MR controller 116 that then computes an MR image, which may be displayed to the user. Alternatively, separate MR transmitter and receiver coils may be used. Images acquired using the MRI apparatus 102 may provide radiologists and physicians with a visual contrast between different tissues and detailed internal views of a patient's anatomy that cannot be visualized with conventional x-ray technology.

The MRI controller 116 may control the pulse sequence, i.e., the relative timing and strengths of the magnetic field gradients and the RF excitation pulses and response detection periods. The MR response signals are amplified, conditioned, and digitized into raw data using a conventional image-processing system, and further transformed into arrays of image data by methods known to those of ordinary skill in the art. Based on the image data, a treatment region (e.g., a tumor) is identified. The image-processing system may be part of the MRI controller 116, or may be a separate device (e.g., a general-purpose computer containing image-processing software) in communication with the MRI controller 116. In some embodiments, one or more ultrasound systems 120 or one or more sensors 122 are displaced within the bore 106 of the MRI apparatus 102 as further described below.

Figure 1B:
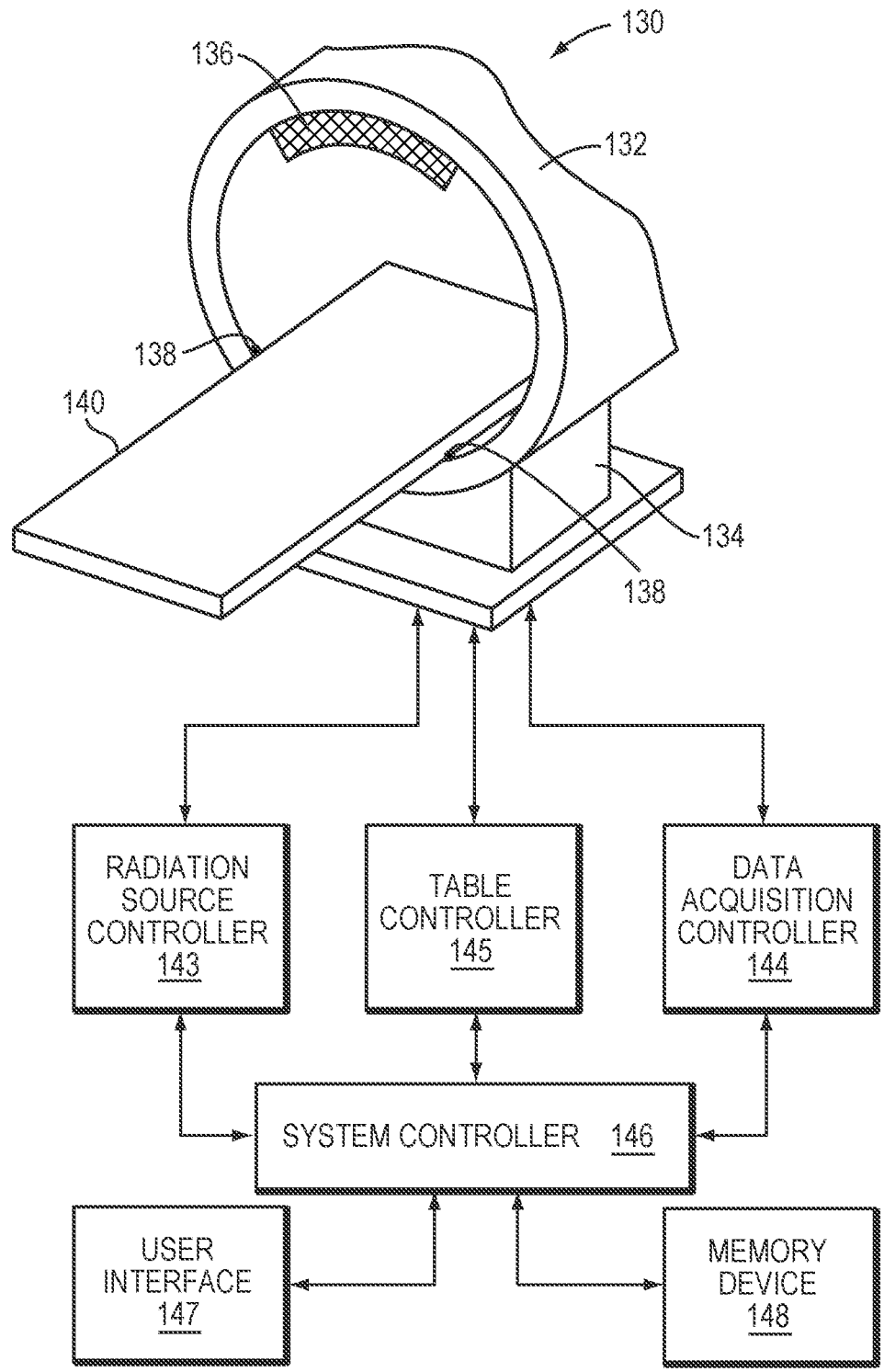
FIG. 1B schematically depicts an exemplary CT system in accordance with various embodiments of the current invention.

FIG. 1B illustrates an exemplary CT system 130 in accordance with embodiments of the present invention. The CT system 130 includes a scanner 132 having a support structure 134, an x-ray source 136, and an x-ray detector 138 on the same or opposite side of the source 136. The scanner 132 is configured to receive a table 140 for a patient to be scanned. The table 140 can be moved through an aperture in the scanner 132 to appropriately position the patient in an imaging volume or plane scanned during imaging sequences. The CT system 130 further includes a radiation source controller 143, a data acquisition controller 144, and a table controller 145. The radiation source controller 143 regulates timing for discharges of x-ray radiation from the x-ray source 136 toward the patient. The data acquisition controller 144 communicates with the x-ray detector 138 to measure the x-ray intensity data transmitted through or reflected from the patient. The acquired intensity data is processed by the data acquisition controller 144 or a system controller 146 for CT image reconstruction. The table controller 145 serves to adjust the table position during or between imaging sequences, depending upon the employed imaging protocol. The controllers 143, 144, 145, 146 may be separate units or may be integrated as a single unit.

In addition, the system controller 146 may be coupled to a user interface 147 and a memory device 148. The user interface 147 may be integrated with the system controller 146, and will generally include a user workstation for initiating imaging sequences, controlling such sequences, and manipulating data acquired during imaging sequences. The memory devices 148 may be local to the imaging system, or partially or completely remote from the system, and may be configured to receive raw, partially processed or fully processed data for CT image reconstruction.

During a typical CT scan, the x-ray scanner 132 rotates around the patient with a predetermined speed, and the x-ray source 136 emits narrow beams of x-rays through the body. The x-ray intensities transmitted through or reflected from the patient at various angles with respect to the patient's body are measured by the detector 138. A two-dimensional tomographic image (i.e., a "slice") of the patient can be created based on the detected beam angles and intensities of the x-rays. Multiple "slices" obtained at different angles can then be processed to reconstruct a CT image. In some embodiments, the CT image of the patient is acquired at a planning stage, i.e., prior to a thermal treatment, to allow time for the treatment plan to be prepared.

Figure 1C:
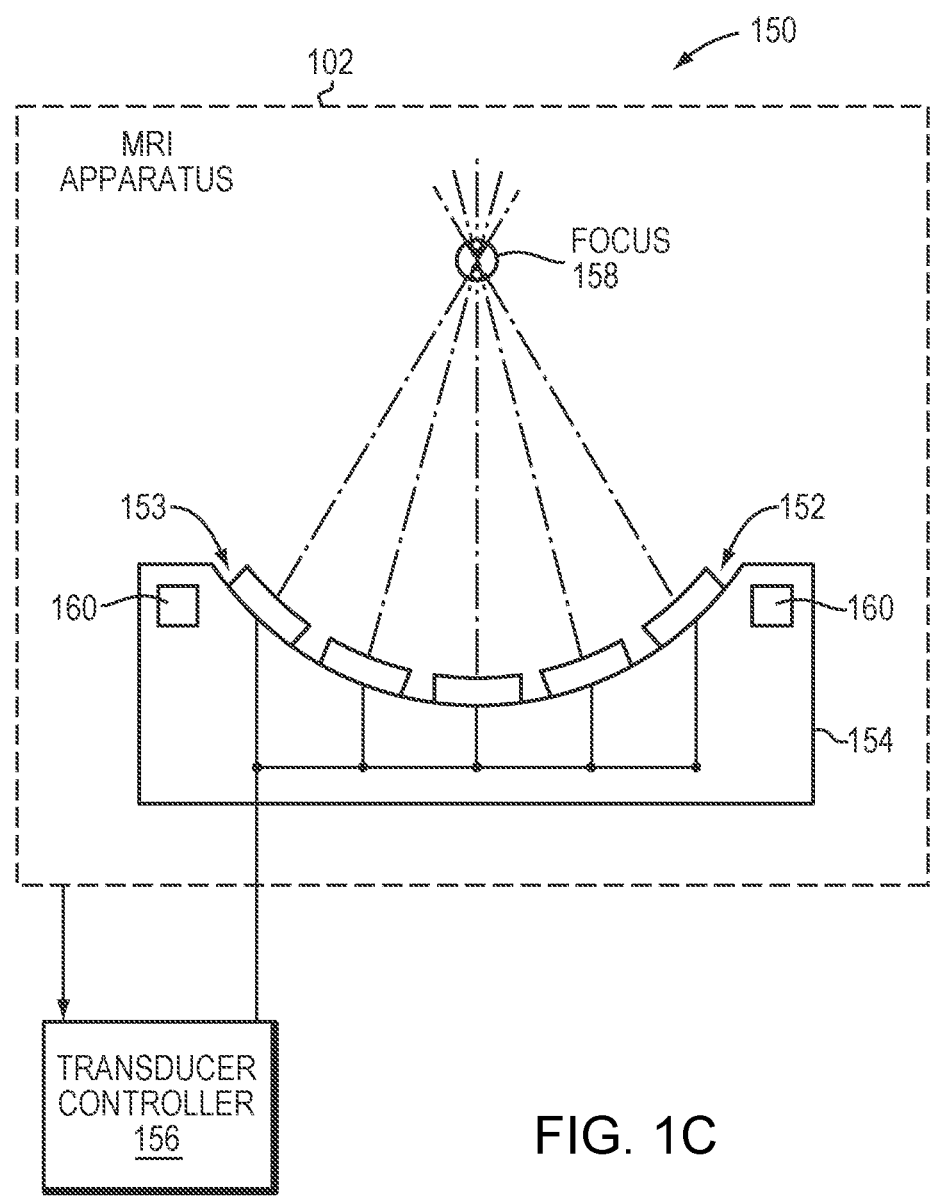
FIG. 1C schematically depicts an exemplary ultrasound system in accordance with various embodiments of the current invention.

FIG. 1C illustrates an exemplary ultrasound system 150 in accordance with some embodiments of the present invention. As shown, the ultrasound system includes a plurality of ultrasound transducer elements 152, which are arranged in an array 153 at the surface of a housing 154. The array may comprise a single row or a matrix of transducer elements 152. In alternative embodiments, the transducer elements 152 may be arranged without coordination, i.e., they need not be spaced regularly or arranged in a regular pattern. The array may have a curved (e.g., spherical or parabolic) shape, as illustrated, or may include one or more planar or otherwise shaped sections. Its dimensions may vary, depending on the application, between millimeters and tens of centimeters. The transducer elements 152 may be piezoelectric ceramic elements. Piezo-composite materials, or generally any materials capable of converting electrical energy to acoustic energy, may also be used. To damp the mechanical coupling between the elements 152, they may be mounted on the housing 154 using silicone rubber or any other suitable damping material.

The transducer elements 152 are separately controllable, i.e., they are each capable of emitting ultrasound waves at amplitudes and/or phases that are independent of the amplitudes and/or phases of the other transducers. A transducer controller 156 serves to drive the transducer elements 152. For n transducer elements, the controller 156 may contain n control circuits each comprising an amplifier and a phase delay circuit, each control circuit driving one of the transducer elements. The controller 156 may split an RF input signal, typically in the range from 0.1 MHz to 4 MHz, into n channels for the n control circuits. It may be configured to drive the individual transducer elements 152 of the array at the same frequency, but at different phases and different amplitudes so that they collectively produce a focused ultrasound beam. The transducer controller 156 desirably provides computational functionality, which may be implemented in software, hardware, firmware, hardwiring, or any combination thereof, to compute the required phases and amplitudes for a desired focus location 158. In general, the controller 156 may include several separable apparatus, such as a frequency generator, a beamformer containing the amplifier and phase delay circuitry, and a computer (e.g., a general-purpose computer) performing the computations and communicating the phases and amplitudes for the individual transducer elements 152 to the beamformer. Such systems are readily available or can be implemented without undue experimentation.

To perform ultrasound imaging, the controller 156 drives the transducer elements 152 to transmit acoustic signals into a region being imaged and to receive reflected signals from various structures and organs within the patient's body. By appropriately delaying the pulses applied to each transducer element 152, a focused ultrasound beam can be transmitted along a desired scan line. Acoustic signals reflected from a given point within the patient's body are received by the transducer elements 152 at different times. The transducer elements can then convert the received acoustic signals to electrical signals which are supplied to the beamformer. The delayed signals from each transducer element 152 are summed by the beamformer to provide a scanner signal that is a representation of the reflected energy level along a given scan line. This process is repeated for multiple scan lines to provide signals for generating an image of the prescribed region of the patient's body. Typically, the scan pattern is a sector scan, wherein the scan lines originate at the center of the ultrasound transducer and are directed at different angles. A linear, curvilinear or any other scan pattern can also be utilized.

The ultrasound system 150 may be disposed within the bore 106 of the MRI apparatus 102 or placed in the vicinity of the MRI apparatus 102. The combined MRI-ultrasound system is known to be capable of monitoring the application of ultrasound for treatment and/or safety purposes. To determine the relative position of the ultrasound system 150 and MRI apparatus 102, the ultrasound system 150 may further include MR trackers 160 associated therewith, arranged at a fixed position and orientation relative to the system 150. The trackers 160 may, for example, be incorporated into or attached to the ultrasound system housing. If the relative positions and orientations of the MR trackers 160 and ultrasound system 150 are known, MR scans that include, in the resulting images, the MR trackers 160 implicitly reveal the location of the ultrasound system 150 in MRI coordinates (in the coordinate system of the MRI apparatus 102). To aid in relating the ultrasound coordinate system to the MRI coordinate system, in some embodiments, an MR image including at least a portion (e.g., some transducer elements) of the ultrasound system 150 is acquired. This MR image may be used in combination with the known spatial arrangement of the ultrasound transducer elements to determine the locations of the transducer elements (not all of which need be included in the acquired MR image) in the MRI coordinate system as further described below.

While penetrating the patient, ultrasound waves typically encounter multiple layers of tissues, e.g., bone, muscle, or fat, whose density and structure, and, consequently, ultrasound propagation properties differ. Due to inhomogeneities and anisotropies in the tissues, the ultrasound wave fronts are often distorted. Moreover, signals from different transducer elements may encounter different thicknesses and contours of materials, and possibly air-filled or liquid-filled pockets between transducer elements and the region to be imaged or treated, resulting in different phase shifts and attenuations. Knowledge of the structure, density, and/or thickness of the multi-layer tissue structures is thus important for compensating for these effects by appropriate phase shifts and amplification factors imposed on the transducer elements, and for avoiding deterioration of focusing properties. While MRI generally provides high-sensitivity images of soft tissue (e.g., the brain), the CT scan creates images with more details about bony structures (e.g., the skull). Accordingly, it may be beneficial to combine image information obtained from the MRI apparatus 102 and CT system 130. To do so, of course, requires registration of the images and, therefore, registration of the MRI and CT coordinate systems.

Figure 2A:
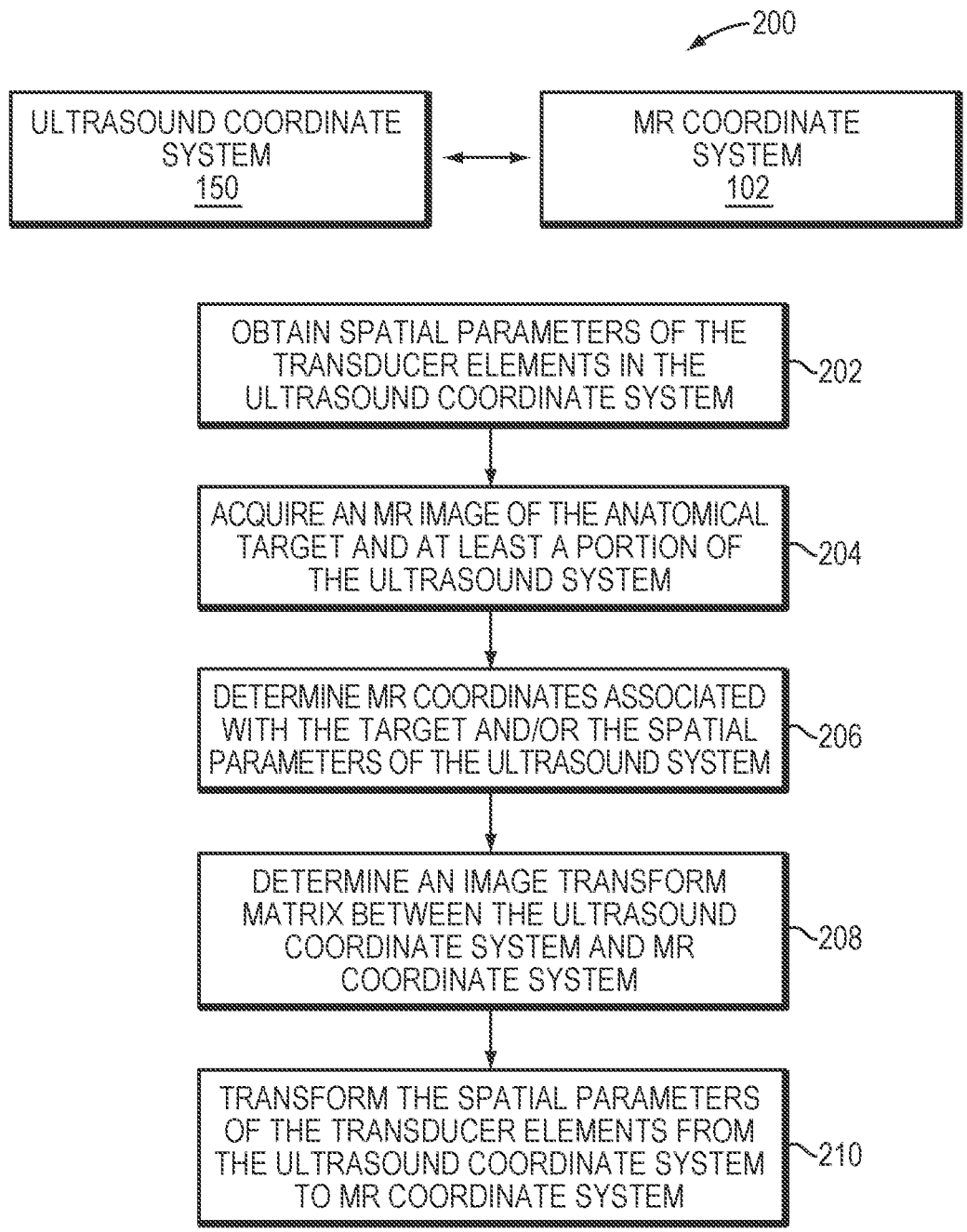
FIG. 2A depicts an approach for correlating the ultrasound coordinate system to MRI coordinate system in accordance with various embodiments of the current invention.

Numerous conventional approaches to image registration are available. In various embodiments, the accuracy of the image registration obtained using any desired approach is verified and evaluated using two imaging modalities, e.g., the ultrasound system 150 in combination with the MRI apparatus 102. FIG. 2A depicts an approach 200 for relating the ultrasound coordinate system 150 to the MRI coordinate system 102. In a first step 202, spatial parameters, such as the orientations and positions, characterizing the transducer elements 152 in the ultrasound coordinate system are obtained using any suitable approach. For example, each transducer element 152 may emit a pulse towards a sensor (not shown) located at the focus 158 or other position; the distance between each transducer element 152 and the sensor may be determined based on the time of flight. The actual location and/or orientation of each transducer element in the ultrasound coordinate system 150 can be determined using this determined distance. The spatial arrangement of the transducer elements may be stored in a memory. In a second step 204, an MR image of an anatomic target of interest (e.g., the patient's head, including the brain and skull) and at least a portion of the ultrasound system (e.g., at least some elements 152 of the transducer array 153) is acquired. In a third step 206, the MRI coordinates associated with the anatomic target and/or the spatial parameters of the portion of transducer elements 152 acquired in the MR image are determined. In a fourth step 208, based on the spatial parameters of the transducer elements 152 in ultrasound coordinate system 202 (obtained in the first step 202) and in the MRI coordinate system 204 (obtained in the second step 204), an image transformation matrix between the two coordinate systems is generated. In a fifth step 210, the transformation matrix is applied to transform the spatial parameters associated with the entire group of transducer elements (or at least a larger portion thereof than the portion acquired in the MR image) from the ultrasound coordinate system to MRI coordinate system. As a result of these operations, the spatial parameters associated with the transducer elements 152 are represented in the MRI coordinate system.

Figure 2B:
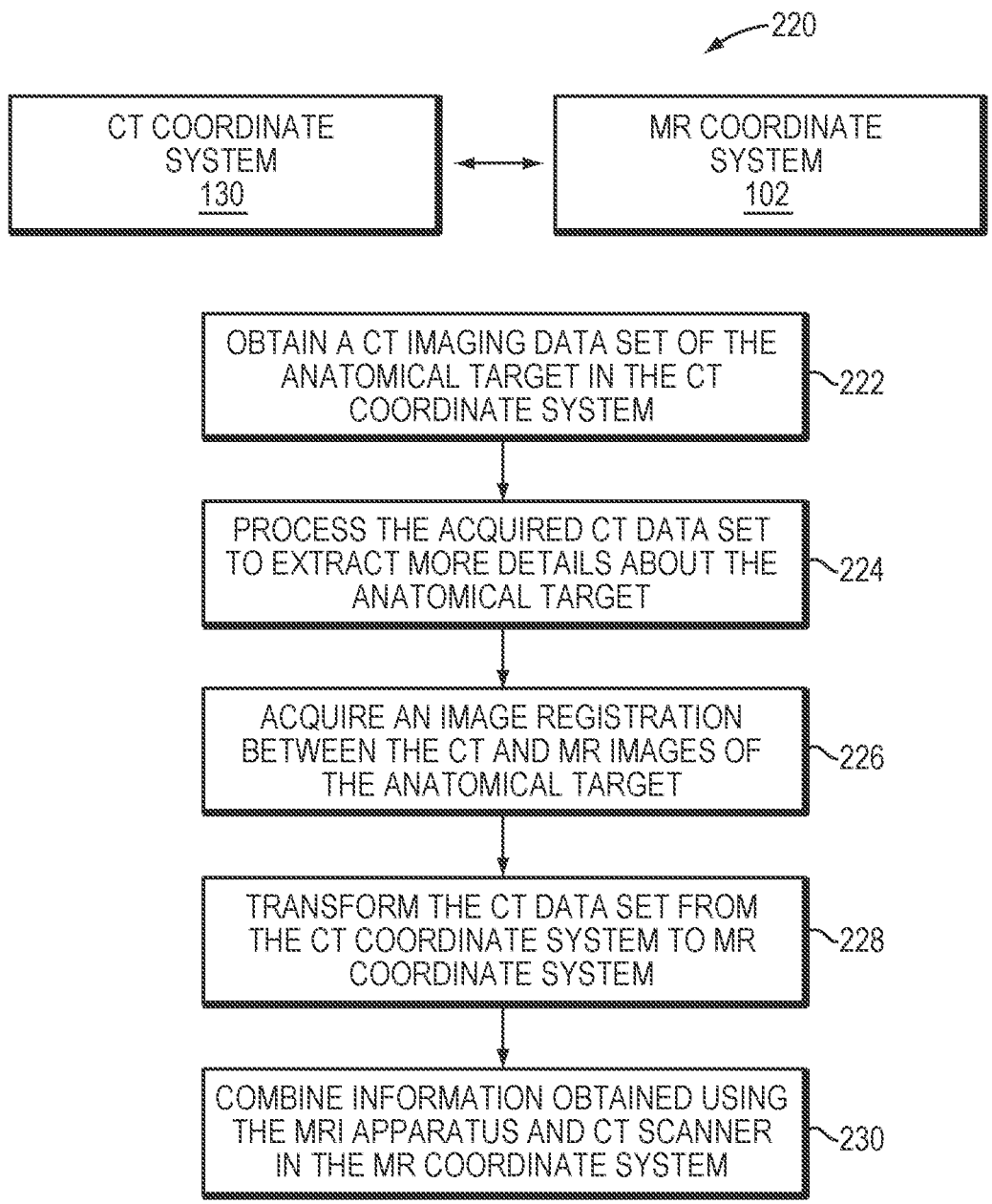
FIG. 2B depicts an approach for correlating the CT system to MRI coordinate system in accordance with various embodiments of the current invention.

FIG. 2B depicts an approach 220 for transforming a CT imaging data set of the anatomic target from the CT coordinate system 130 to MRI coordinate system 102. In a first step 222, the CT imaging data set is acquired during a treatment planning stage or prior to the treatment stage. In some embodiments, the acquired CT data set is processed to extract more details about the anatomic target (step 224). For example, the CT image may include a bony structure such as a skull; the skull may be segmented by applying a thresholding technique and/or other known imaging processing to the acquired density values of the CT data set to determine the surface of the skull. Thereafter, a conventional proposed approach may be utilized to acquire an image registration between the CT and MR images of the anatomic target (step 226). Based on the obtained MRI-CT image registration, the CT data set, including the extracted details of the anatomic target, may be transformed from the CT coordinate system to the MRI coordinate system (step 228). Information obtained using the MRI apparatus 102 and CT scanner 130 can then be combined in the MRI coordinate system to provide improved imaging quality or additional information about the anatomic target (step 230). This approach is particularly useful when the target of interest includes both soft and bony tissues—the MRI provides high-sensitivity images of the soft tissue (e.g., a brain) while the CT scan provides details about the bony structure (e.g., a skull).

Figure 2C:
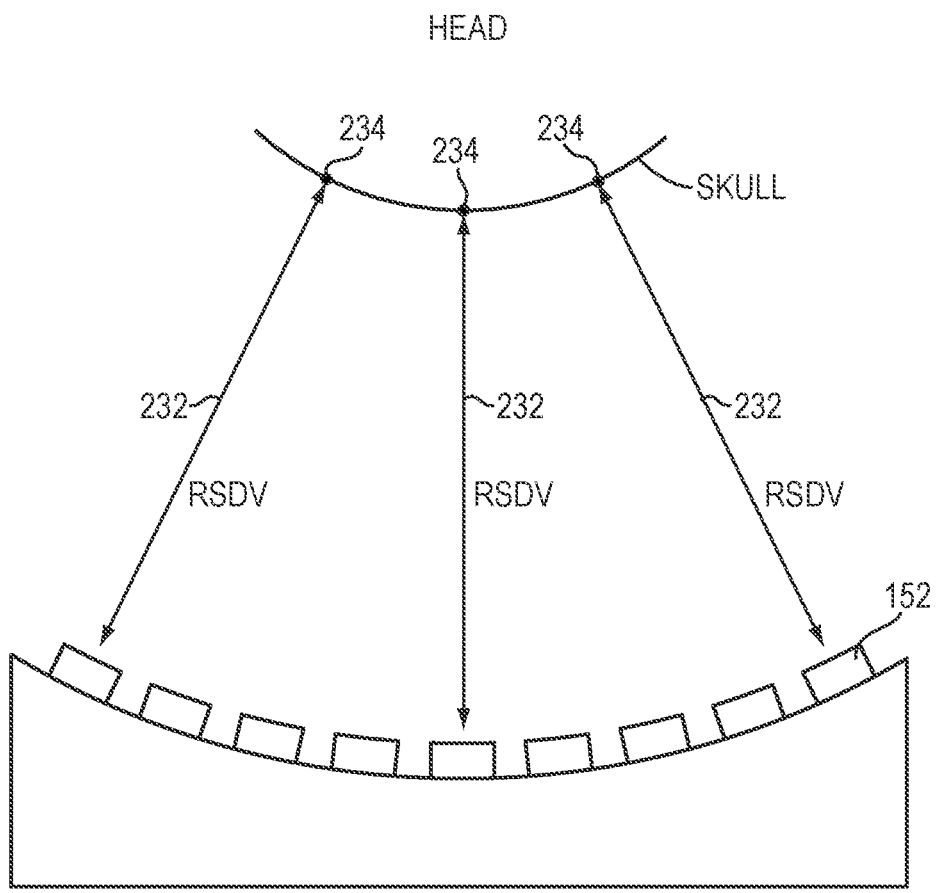
FIG. 2C depicts an approach for computing a distance between each transducer element and the closest point on a reflective surface of the target in accordance with various embodiments of the current invention.

Once the spatial parameters of the transducer elements and information acquired using the CT scan are both transformed to coordinates in the MRI coordinate system, the accuracy of the MRI-CT image registration may be evaluated. Referring to FIG. 2C, in which the anatomic target of interest is the patient's head, the distance 232 between each transducer element 152 and the closest point 234 on the skull surface to the transducer element 152 can be computed in the MRI coordinate system 102. The computed distance 232 is denoted as a registration skull distance vector ("RSDV").

Figure 3A:
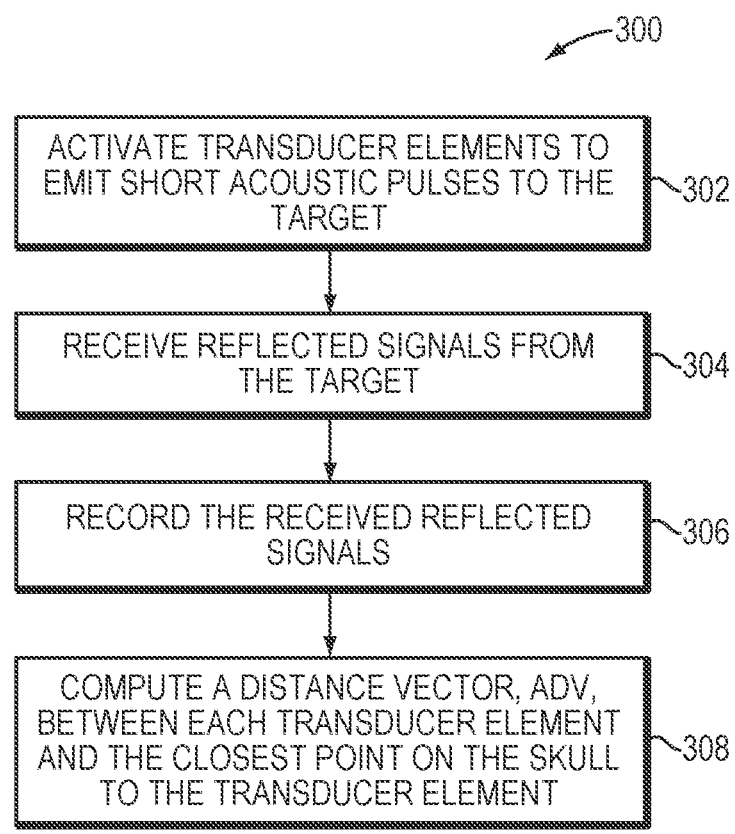
FIG. 3A depicts an approach for acoustically measuring a distance between each transducer element and the closest point on a reflective surface of the target in accordance with various embodiments of the current invention.

FIG. 3A illustrates acoustic measurement of this distance using a time-of-flight approach 300—i.e., based on the timing of signals transmitted from and received by the transducer elements 152 and the known speed of sound in the medium in which the ultrasound system is operated (e.g., in water or air). For example, in one implementation, all (or more than 50%) of the transducer elements are set in a transmission mode to emit short acoustic pulses (~50 μs) towards the skull (step 302). Substantially immediately after the pulse emission (e.g., a few micro-seconds after), at least some of the transducer elements are switched to a receiving mode to receive signals reflected from the skull (step 304).

In one embodiment, the signals received by all receiver transducer elements are recorded simultaneously (step 306). In another embodiment, the transducer elements are grouped into multiple subsets; each subset is sequentially activated to emit and receive signals as described above, and the received signals are sequentially recorded until signals from the desired sets of transducer elements are included. The recorded signals can be processed to compute a distance vector (or acoustic distance vector, "ADV") between each transducer element 152 and the nearest point on the skull to the transducer element 152 (step 308).

Figure 3B:
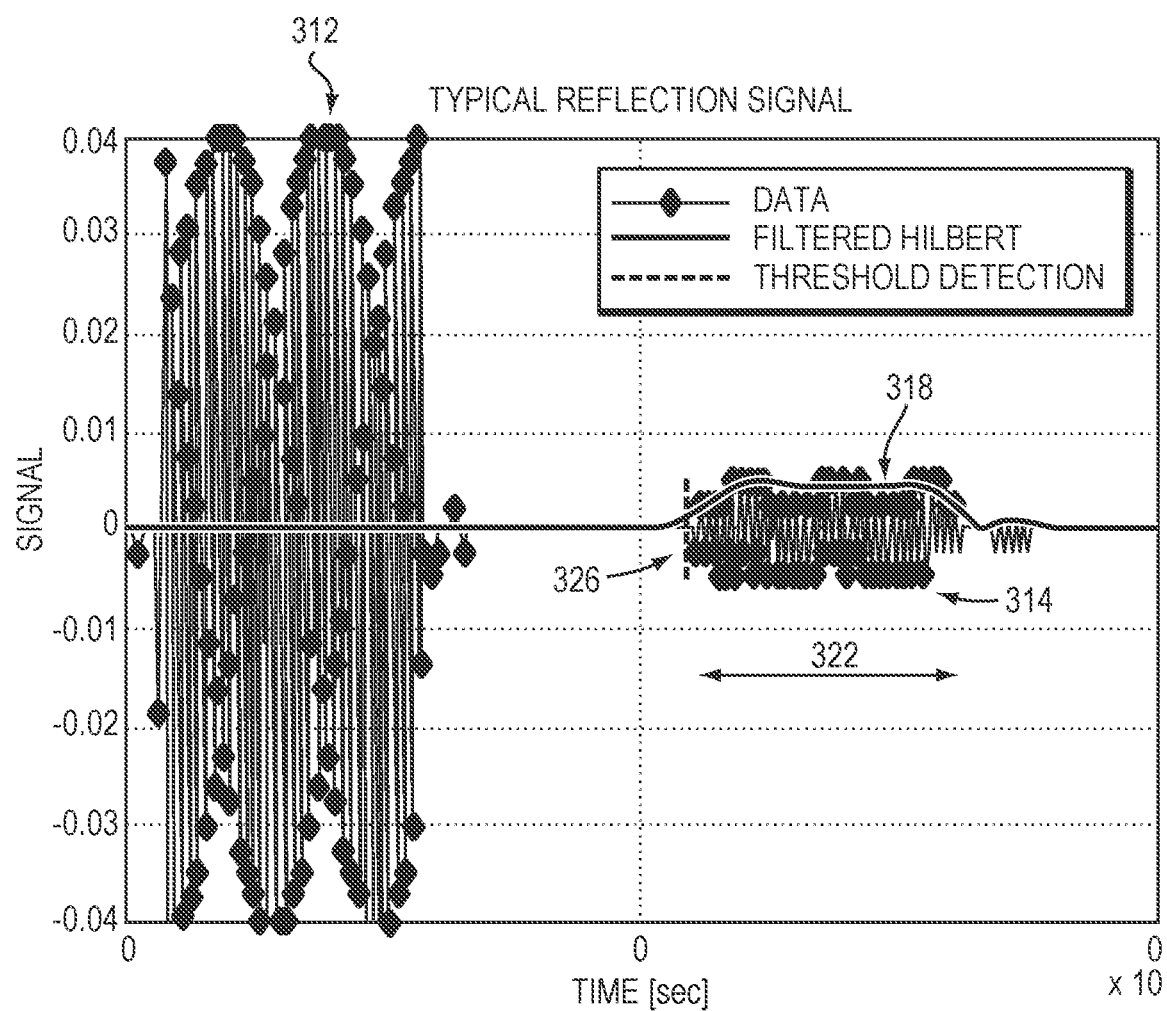
FIG. 3B depicts the waveforms of signals transmitted from and received by the ultrasound system accordance with various embodiments of the current invention.
Figure 3C:
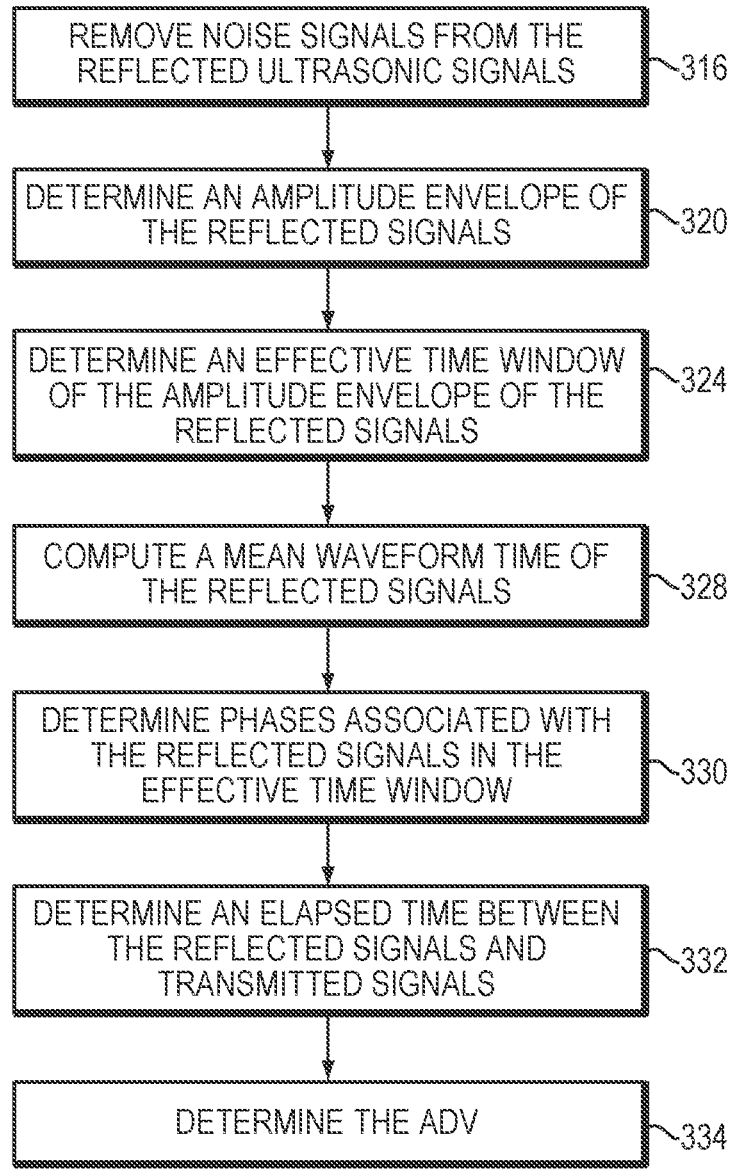
FIG. 3C depicts signal processing for determining a distance between each transducer element and the closest point on a reflective surface of the target in accordance with various embodiments of the current invention.

FIG. 3B depicts the recorded waveforms of typical ultrasound signals, where waveforms 312 represent the transmitted signals, which may be used as references for phase measurements of the reflected signals having waveforms 314. The recorded signals may be processed to determine the ADV. For example, also referring to FIG. 3C, the signals may be filtered at a central ultrasonic frequency (e.g., 650 KHz) with a range of 100 KHz to remove noise signals from the ultrasonic signals (step 316). An envelope-detection approach (e.g., a Hilbert transform) may then be applied to the filtered signals to determine an amplitude envelope 318 of the reflected signals 314 (e.g., in the time window between 70 and 200 µs shown in FIG. 2C) (step 320). An effective time window 322 of the amplitude envelope 318 may then be determined (step 324). For example, the starting time and stopping time of the amplitude envelope 318 may be determined when the signal amplitude is above a predetermined amplitude threshold 326 and below the predetermined amplitude threshold 326, respectively. A mean waveform time of the reflected signals 314 can then be calculated (e.g., integrating the signals over the determined effective time window) (step 328). In addition, phases associated with the reflected signals 314 in the effective time window 320 may be obtained based on the reference phases of the transmitted signals 312 (step 330). Based on the determined mean waveform time and phases associated with the reflected signals 314, an elapsed time between the reflected signals 314 and transmitted signals 312 can be computed (step 332). The ADV between each transducer element 132 and the nearest reflector to the transducer element 132 can then be determined (step 334) based on the elapsed time and the speed of sound in the media. The measured ADV may be transformed from the ultrasound coordinate system to MRI coordinate system using the ultrasound-MRI transformation matrix obtained as shown in FIG. 2A. In this example, because the external surface of the skull reflects the largest fraction of the ultrasound waves (reflections from other interlayer skull surfaces are negligible), the nearest reflector is the closest point on the external skull surface. Generally, the ADV measured using this approach has a high accuracy (on the order of one-tenth of the wavelength (i.e., 0.25 mm) at the central frequency) and can thus be suitable for evaluating the image registration obtained conventionally and/or detecting patient movement.

Figure 4:
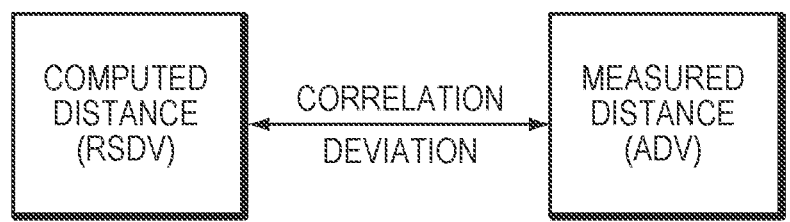
FIG. 4 depicts an approach for evaluating the accuracy of an image registration obtained using a conventional approach in accordance with various embodiments of the current invention.

Referring to FIG. 4, the computed distance (RSDV) may be compared to the acoustically measured distance (ADV) to evaluate the accuracy of the image registration obtained using a conventional approach. In one embodiment, for each individual transducer element that is activated for an ADV measurement, a comparison between the RSDV and ADV is made; the comparison may be quantified as a correlation score and/or a discrepancy between the RSDV and the ADV using any suitable approach capable of comparing two vectors (such as an error function as further described below). The quantified comparison values for all (or at least some) transducer elements that are activated for the ADV measurement are then added together to represent the "entire" correlation/discrepancy between the RSDV and the ADV for all (or at least some) transducer elements. Because both the acoustic measurement of ADV and computation of RSDV in the MRI coordinate system can be determined with high accuracy, the deviation and/or correlation score indicates the accuracy of the MRI-CT image registration—a smaller deviation or higher correlation score indicates a higher accuracy of the MRI-CT image registration.

The distance vectors, RSDV and ADV, may be compared using any suitable approach. For example, a simple error function between the two distance vectors may be calculated as follows:

$$Err(x_{shift}, y_{shift}, z_{shift}) = \sum_{i=1}^{Nel} (X_{regi} - X_{refi} - x_{shift})^2 + \qquad \text{eq. (1)}$$
$$(Y_{regi} - Y_{refi} - y_{shift})^2 + (Z_{regi} - Z_{refi} - z_{shift})^2,$$

where $X_{regi}$, $Y_{regi}$, and $Z_{regi}$ represent the values of RSDV for each transducer element i, and $X_{refi}$, $Y_{refi}$, and $Z_{refi}$ represent the values of ADV for each transducer element i; $x_{shift}$, $y_{shift}$, and $z_{shift}$ represent global shift values that may be varied to obtain a minimal value of the error function; and Nel represents the number of transducer elements that are activated for an ADV measurement. The error function is used to evaluate the accuracy of the image registration. For example, if the minimal value of the error function cannot be found, or if the minimal value is above a predetermined threshold, the image registration is inaccurate (or at least not sufficiently accurate for medical treatment purposes). In some embodiments, each transducer element 152 is allowed to have an average error below 3 mm for registration verification purposes; accordingly, in an exemplary ultrasound system having 1000 transducer elements, the threshold value for determining the verification of the image registration is set as $10^4$ mm$^2$. This value can be adjusted based on the allowable error for each transducer element. Although a distance may sometimes be miscalculated for the transducer elements (e.g., due to measurement noise, etc.), because the foregoing approach evaluates the image registration by the use of a large number of transducer elements (e.g., on the order of a thousand), a small number of miscalculated elements may not significantly affect the minimal value of the error function. Accordingly, a high error value occurs only when the RSDV and ADV are inconsistent or corrupted.

Figure 5A:
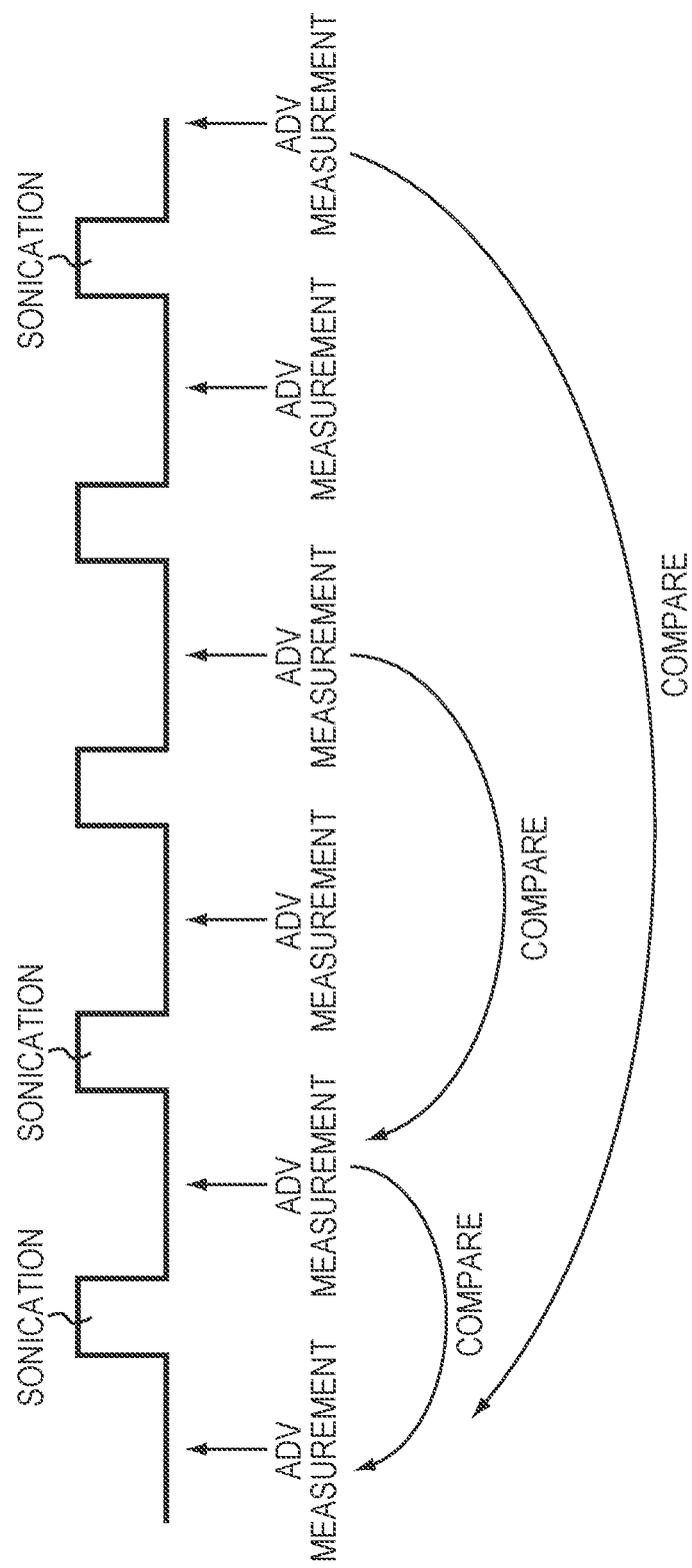
FIGS. 5A and 5B depict various approaches to detecting patient's movement during treatment in accordance with various embodiments of the current invention.

In various embodiments, the time evolution of ADV and/or comparison between the ADV and RSDV during thermal treatment may be used to detect movement of the patient. As used herein, the term "during treatment" connotes the overall time of a treatment session and generally includes the time prior to, during, and after each sonication. Referring to FIG. 5A, in various embodiments, each time prior to, during, and/or after sonication, a new ADV is measured in real time. Because the new ADV may be measured from subsets of the transducer array and/or with a lower quality, the ADV measuring period may be short enough (e.g., 200 µs) to be interleaved with the treatment period without interruption thereof. Alternatively, one or more subsets of the transducer array 153 may be dedicated to ADV measurements while the remainder of the array 153 focuses ultrasound for treatment purposes. Further, a separate ultrasound transducer array of elements (or, again, one or more subsets of the elements of the transducer array 153)

may be provided to receive signals reflected from the skull for ADV measurements. The receiving transducers, if separate, may be disposed in the vicinity of the ultrasound transducer array 153, or integrated into its housing 154. In addition, the transducer array may be disposed within the bore 106 of the MRI apparatus 102 or placed in the vicinity thereof.

The newly measured ADV may then be compared to the ADV obtained at an earlier time during treatment (e.g., prior to any sonication being performed, a plurality of sonications before, or one sonication before). If the new ADV deviates significantly from the previously obtained ADV, the patient has likely moved in the interim. In various embodiments, when the deviation is above a threshold (e.g., 5,000 mm$^2$ for 1000 transducer elements or each transducer element having an average error of 2.2 mm, or in percentage terms, more than 5% or 10%), the patient's movement is considered significant and corrective action may be performed to confirm and/or compensate for the movement.

In some embodiments, the time evolution of ADV during treatment is monitored to anticipate the patient's movement. For example, for a treatment involving 1000 transducer elements, if the ADV increases by 550 mm$^2$ during each sonication, it is anticipated that the patient may move beyond what can be clinically tolerated by the tenth sonication. Accordingly, the treatment may be suspended at the end of the ninth sonication to avoid damage to healthy non-target tissue resulting from misalignment of the patient and the ultrasound system.

Figure 5B:
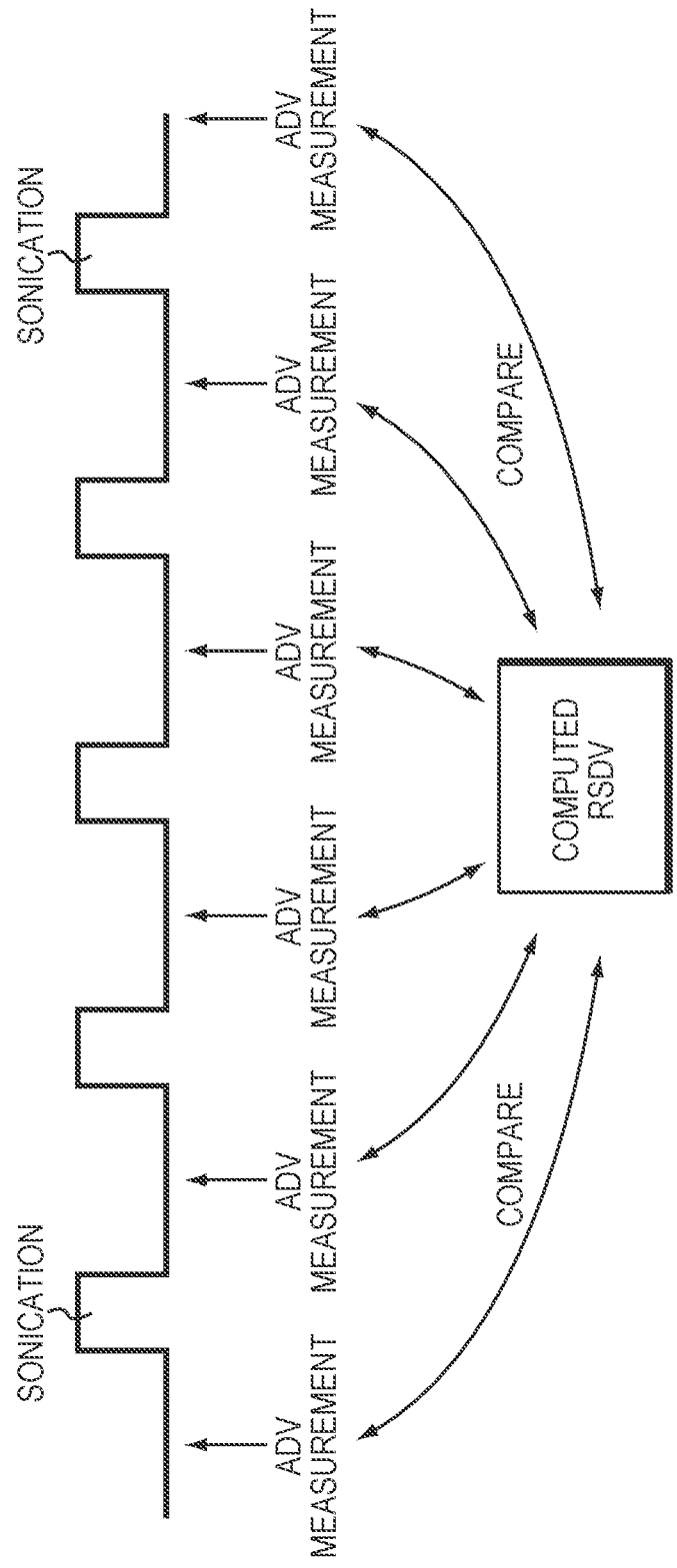

Referring to FIG. 5B, in another embodiment, movement detection is determined based on a comparison between the ADV and the SRDV. For example, after the accuracy of image registration is verified, a new ADV is measured and compared to the RSDV computed using the verified image registration. Again, if the difference between ADV and RSDV is below a threshold (e.g., 5,000 mm$^2$ for 1000 transducer elements), the patient's movement may be considered negligible or within clinically tolerable limits. If, however, the difference between the ADV and the RSDV exceeds the threshold, the patient may have moved significantly and corrective action may be taken.

Figure 6A:
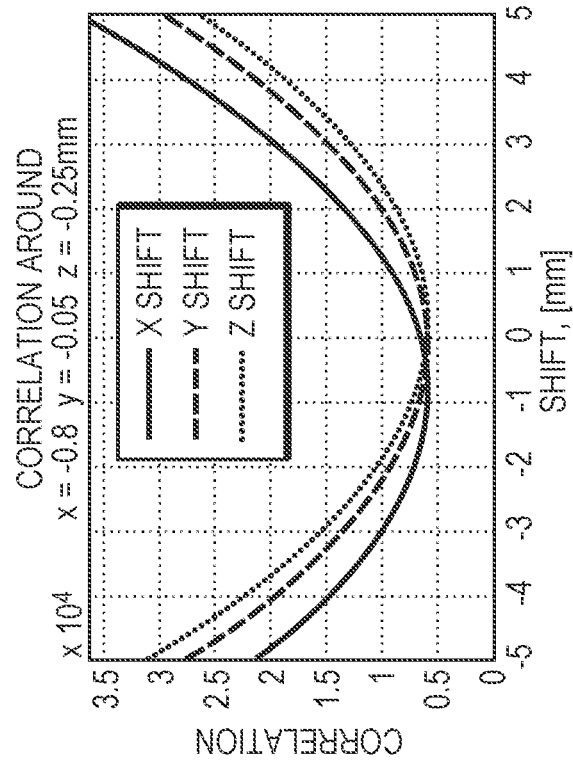
FIGS. 6A and 6B depict exemplary values of the error function for two distance measurements having the same transducer array and target positions at different times in accordance with various embodiments of the current invention.
Figure 6B:
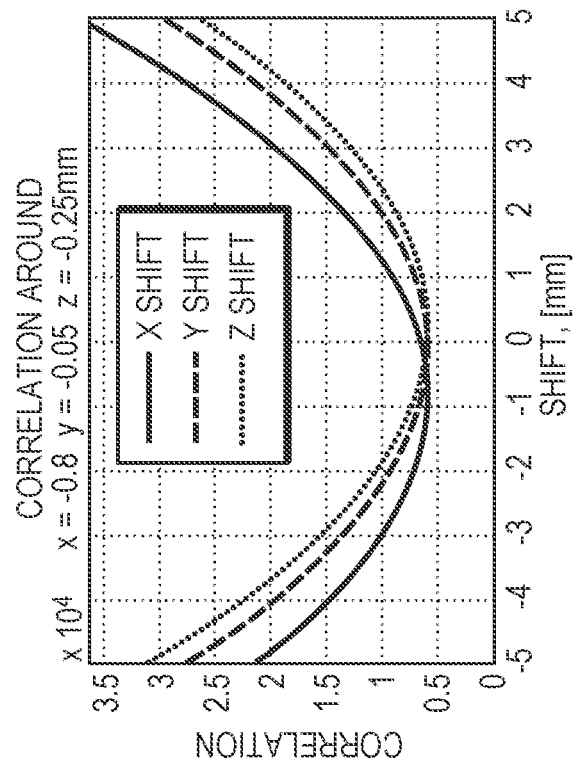
Figure 7A:
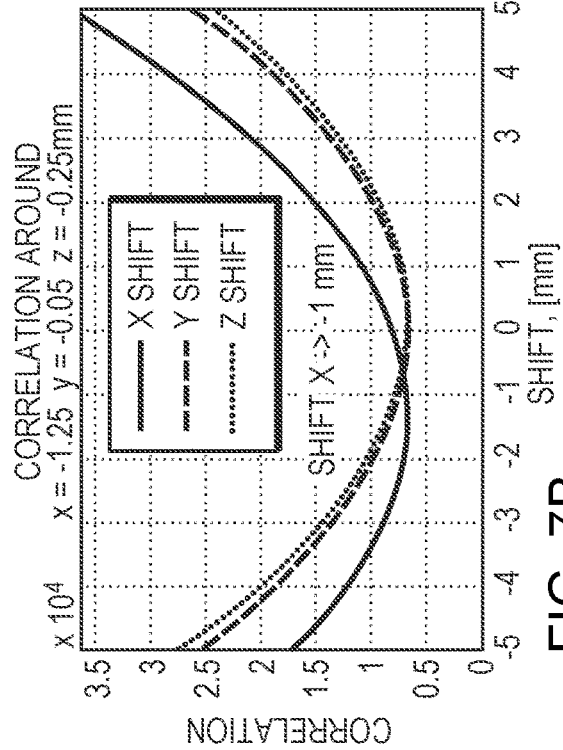
FIGS. 7A-7D depict exemplary values of the error function for four distance measurements having different transducer array and target positions in accordance with various embodiments of the current invention.
Figure 7B:
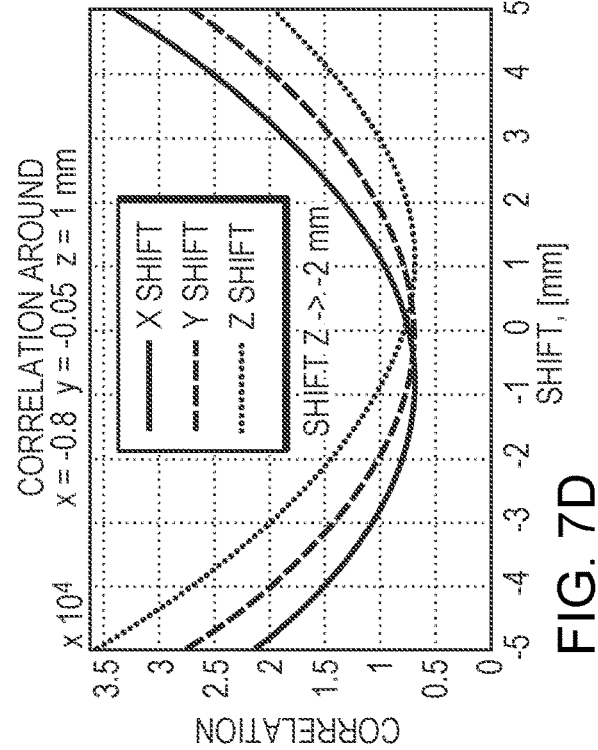
Figure 7C:
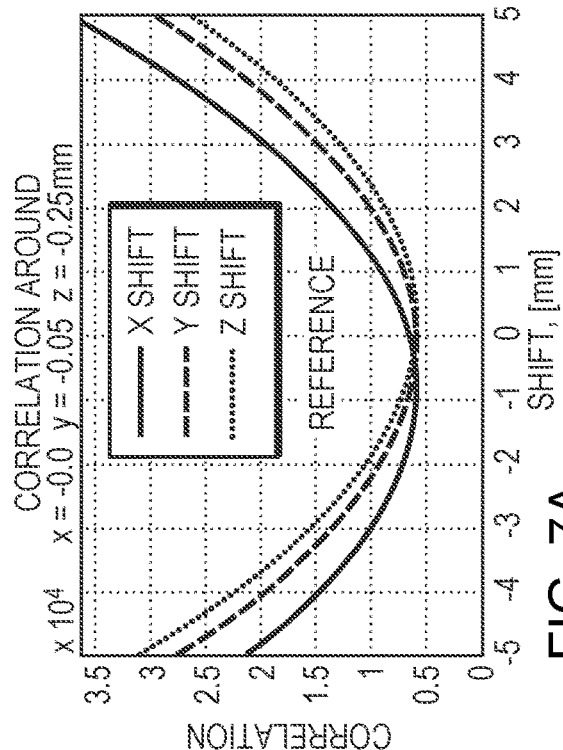
Figure 7D:
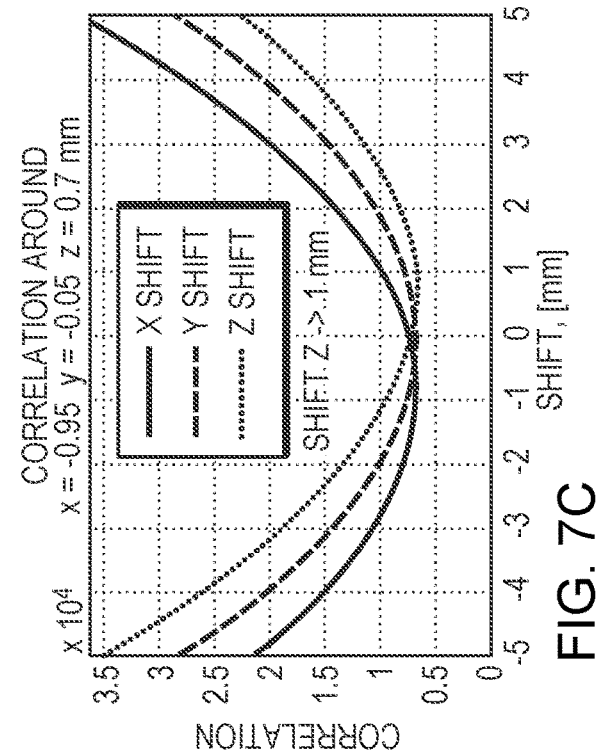

Accordingly, comparing the ADV to the RSDV or to a previously obtained ADV may identify a suspected patient movement without the need for image reconstruction of the target, allowing movement to be detected in real time. The newly measured ADV best matches the computed RSDV (or the previously obtained ADV)—i.e., has the smallest deviation therefrom—when the error function in eq. (1) has a minimal value. Accordingly, patient movement may be detected by monitoring the value and/or the position (i.e., the values of $x_{shift}$, $y_{shift}$, and $z_{shift}$) associated with the minimal value. The sensitivity of movement detection may be adjusted by changing the allowed deviation threshold. FIGS. 6A and 6B depict exemplary values of the error function on the main axes for two repeated ADV measurements using the same image registration (thereby same RSDV) based on the same positions of the transducer array and skull at different times. The similarity between the error values in FIGS. 6A and 6B indicates that the approach of using the minimal value and/or position of the error function to determine the validity of the image registration and/or movement of the patient is reliable and repeatable. If the patient's movement is determined based on the ADV profile (i.e., by comparing the newly measured ADV to a previously obtained ADV), a higher similarity of the minimal values and positions of the error function are expected when there is no patient movement.

FIGS. 7A-7D depict exemplary values of the error function on the main axes for four ADV measurements using the same image registration but with different skull positions. The values and positions of the minimum are shown to vary with the skull position. Accordingly and again, the current invention provides a sensitive, accurate approach to verify the image registration and/or detect patient movement.

As noted, if the comparison indicates that a significantly movement has likely occurred, a corrective action may be performed. The corrective action may include acquiring a new MR image to confirm the movement, suspending the ultrasound treatment, adjusting the positions of the ultrasound system and/or the patient to compensate for the movement, etc. For example, a newly acquired MR image of the anatomic target may be checked against the last valid MR image in order to confirm the movement. This is particularly useful when only some of the transducers in the array 153 are dedicated to measuring the ADV and thereby exhibit lower sensitivity (compared with the ADV measured using the entire transducer array). If the MR image comparison reveals that a movement occurred, the ultrasound treatment may be suspended until the position of the ultrasound system and/or the patient is adjusted. If, however, the MR image comparison shows that a movement either did not occur or was not clinically significant, the treatment proceeds as planned.

Figure 8A:
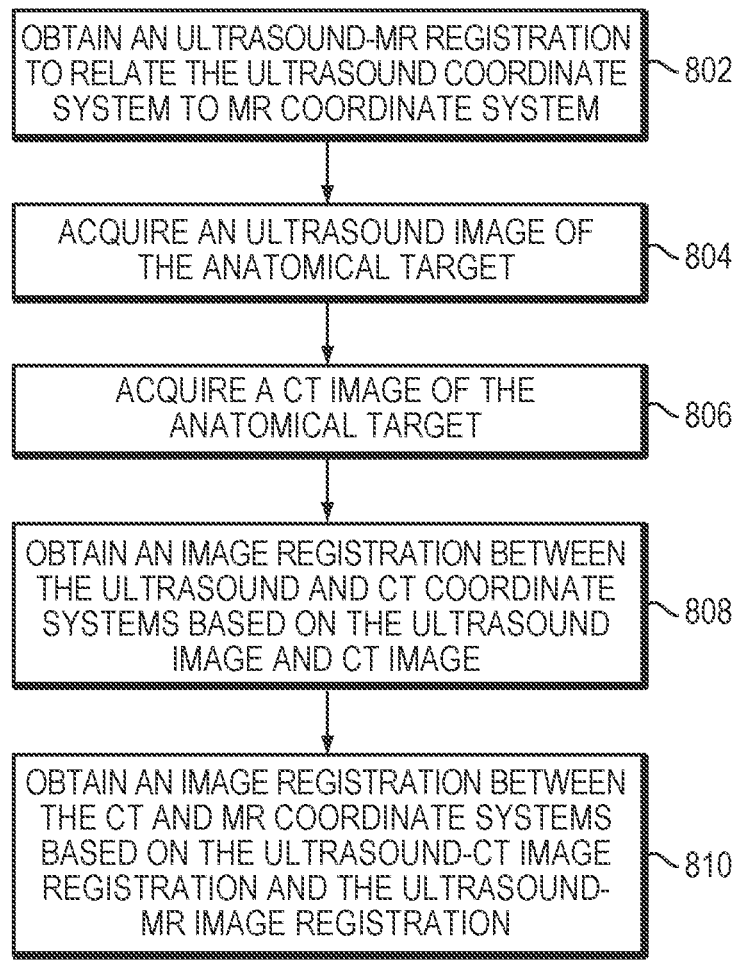
FIGS. 8A-C depict various approaches to registration of two imaging coordinate systems in accordance with various embodiments of the current invention.
Figure 8B:
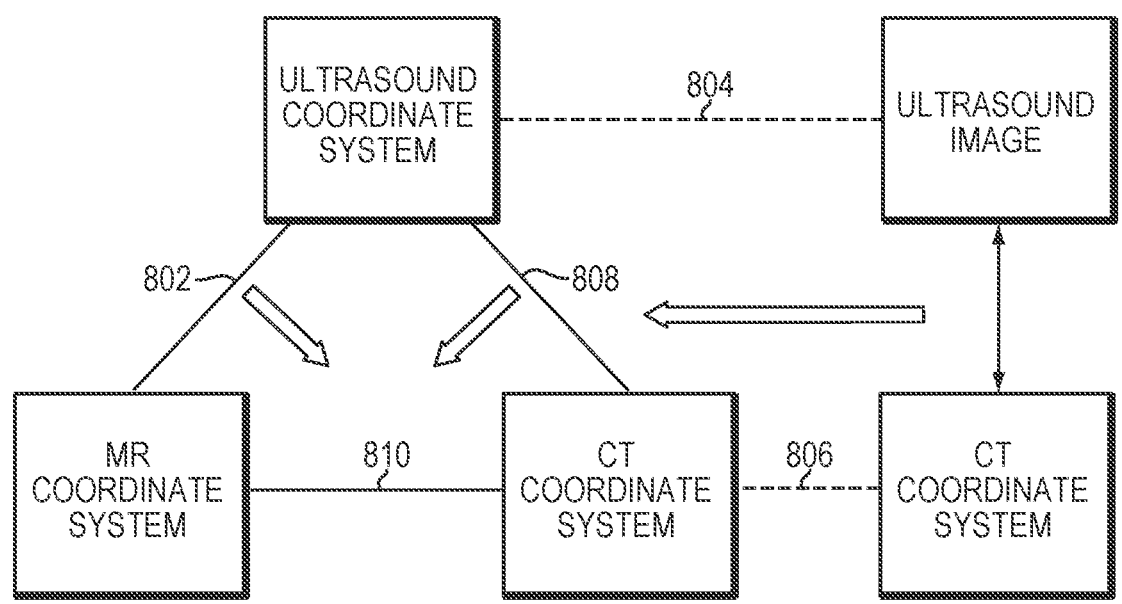

In some embodiments, the combined ultrasound and MRI system provides imaging registration between the MRI and CT coordinate systems with a sufficient accuracy for treatment purposes. With reference to the exemplary embodiment shown in FIGS. 8A and 8B, in a first step 802, the ultrasound coordinate system is first registered to the MRI coordinate system using an MR image of at least a portion of the ultrasound system in combination with information specifying the spatial arrangement of the transducer array in the ultrasound coordinate system as described in connection with FIG. 2A. This ultrasound-MRI registration (which may be expressed, for example, as a transformation matrix) allows the spatial arrangement of the transducer elements to be transformed from the ultrasound coordinate system to the MRI coordinate system. In a second step 804, an ultrasound image of the anatomic target of interest is acquired. In a third step 806, a CT image of the anatomic target of interest is acquired (e.g., uploaded from a computer memory that stores image data previously obtained during the treatment planning stage or prior to the start of treatment). In a fourth step 808, the acquired ultrasound image is compared to the CT image to register the ultrasound and CT images. The ultrasound-CT image registration may be established, for example, by fitting the CT imaging data to the ultrasound imaging data using correlation or any other suitable approach. In a fifth step 810, a transformation (e.g., a transformation matrix) between the CT and MRI coordinate systems is computed by first transforming the CT imaging data from the CT coordinate system to the ultrasound coordinate system (using the ultrasound-CT image registration obtained in the fourth step 808), and subsequently transforming the transformed data from the ultrasound coordinate system to the MRI coordinate system (using the ultrasound-MR image registration obtained in the first step 802). The obtained MRI-CT coordinate transformation thus allows images obtained using the two imaging systems to be combined, and thereby offers details about both the soft tissue and bony structure for accurate and efficient treatment planning.

Figure 8C:
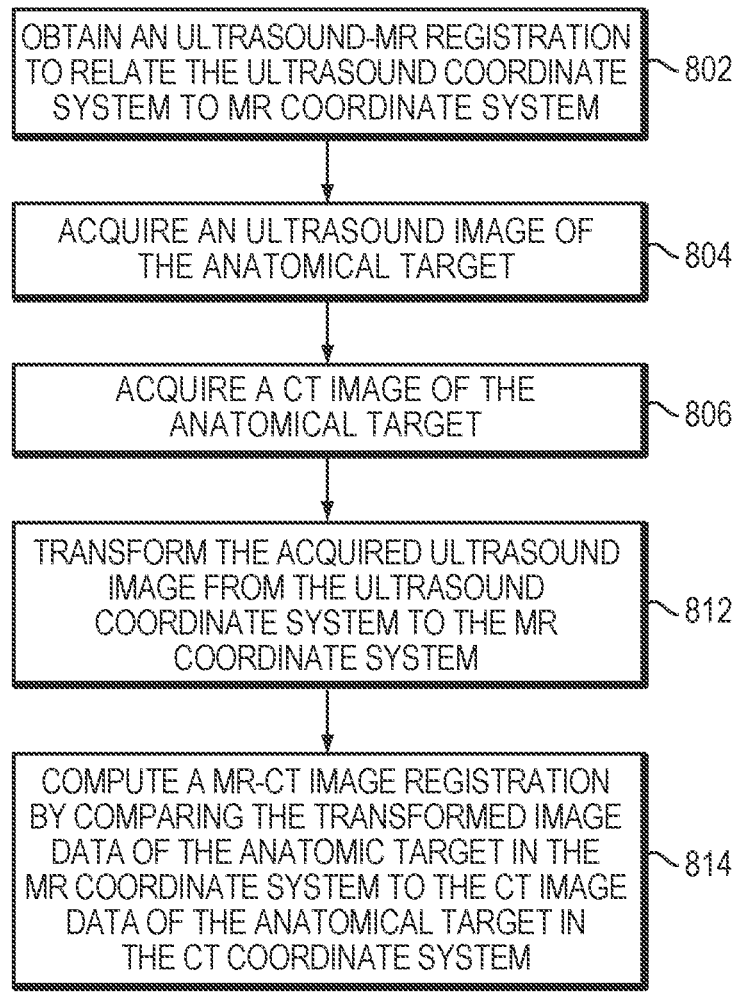

In an alternative embodiment, with reference to FIG. 8C, the ultrasound image of the anatomic target acquired in the second step 804 is transformed from the ultrasound coordinate system to the MRI coordinate system using the transformation matrix obtained in the first step 802 (step 812). The transformed image data of the anatomic target in the MRI coordinate system is then compared to the previously obtained CT image data of the anatomic target in the CT coordinate system to compute an MRI-CT image registration (step 814). This can be achieved by, for example, fitting the CT image data of the anatomic target to the transformed image data of the anatomic target in the MRI coordinate system. Accordingly, the MRI-CT image registration may be conveniently computed as described herein.

Although the invention has been described with reference to the use of an ultrasound system for evaluating and/or obtaining a coordinate transformation relating the MRI and CT coordinate systems and/or detecting the patient's movement, it is not intended for this arrangement to limit the scope of the invention. For example, the MRI coordinate system may be used to register the ultrasound and CT coordinate systems, and similarly, the CT system may be used to register the ultrasound and MRI systems. In addition, other imaging modalities may also be used in lieu of any of the above-described imaging modalities to verify and/or obtain an imaging registration relating any two imaging systems using the approaches described above and/or detect a patient's movement in real time during treatment.

Moreover, it is to be understood that the features of the various embodiments described herein are not necessarily mutually exclusive and can exist in various combinations and permutations, even if such combinations or permutations are not made express herein, without departing from the spirit and scope of the invention. In fact, variations, modifications, and other implementations of what is described herein will occur to those of ordinary skill in the art without departing from the spirit and the scope of the invention.

In general, functionality for evaluating and/or computing an imaging registration between two or more imaging systems and/or detecting the patient's movement as described above, whether integrated with the controllers of MRI, the ultrasound system, and/or the CT scanning system, or provided by a separate external controller, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

What is claimed is:

1. A method for detecting a moving anatomic feature during a treatment sequence having a plurality of treatment periods, the method comprising:
   activating an external image-acquisition device to measure a shortest distance between the anatomic feature and at least a portion of the external image-acquisition device during the treatment sequence;
   comparing the measured shortest distance in a current treatment period to the measured shortest distance in a previous treatment period to determine a deviation therefrom; and
   determining movement of the anatomic feature based on the deviation.

2. The method of claim 1, wherein the shortest distance between the anatomic feature and the at least a portion of the external image-acquisition device is measured based on signals transmitted from and received by the external image-acquisition device.

3. The method of claim 2, further comprising comparing the deviation to a predetermined threshold and determining movement of the anatomic feature based on the comparison.

4. The method of claim 1, wherein the external image-acquisition device comprises an ultrasound transducer system.

5. The method of claim 1, wherein the shortest distance between the anatomic feature and the at least a portion of the external image-acquisition device is measured acoustically.

6. A system for detecting a moving anatomic feature during a treatment sequence having a plurality of treatment periods, the system comprising:
   an external image-acquisition device for measuring a shortest distance between the anatomic feature and at least a portion of the external image-acquisition device during the treatment sequence; and
   a controller in communication with the external image-acquisition device, the controller being configured to:
   compare the measured shortest distance in a current treatment period to the measured shortest distance in a previous treatment period to determine a deviation therefrom; and
   determine movement of the anatomic feature based on the deviation.

7. The system of claim 6, wherein the controller is further configured to measure the shortest distance between the anatomic feature and the at least a portion of the external image-acquisition device based on signals transmitted from and received by the external image-acquisition device.

8. The system of claim 7, wherein the controller is further configured to compare the deviation to a predetermined threshold and determine movement of the anatomic feature based on the comparison.

9. The system of claim 6, wherein the external image-acquisition device comprises an ultrasound transducer system.

* * * * *